United States Patent
Beauglehole et al.

(10) Patent No.: US 8,263,762 B2
(45) Date of Patent: Sep. 11, 2012

(54) ALKOXY-CARBONYL-AMINO-ALKYNYL-ADENOSINE COMPOUNDS AND DERIVATIVES THEREOF AS $A_{2A}R$ AGONISTS

(75) Inventors: Anthony R. Beauglehole, Charlottesville, VA (US); Frank W. Schmidtmann, Charlottesville, VA (US); Jayson M. Rieger, Charlottesville, VA (US); Robert Thompson, Charlottesville, VA (US)

(73) Assignee: Dogwood Pharmaceuticals, Inc., Charlottesville, VA (US)

( * ) Notice: Subject to any disclaimer, the term of this patent is extended or adjusted under 35 U.S.C. 154(b) by 135 days.

(21) Appl. No.: 12/827,932

(22) Filed: Jun. 30, 2010

(65) Prior Publication Data

US 2011/0003766 A1 Jan. 6, 2011

Related U.S. Application Data

(60) Provisional application No. 61/221,692, filed on Jun. 30, 2009.

(51) Int. Cl.
*C07H 19/167* (2006.01)
*C07H 19/173* (2006.01)
*A01N 43/04* (2006.01)
*A61K 31/70* (2006.01)

(52) U.S. Cl. .......................................... 536/27.6; 514/46
(58) Field of Classification Search ........................ None
See application file for complete search history.

(56) References Cited

U.S. PATENT DOCUMENTS

| 6,232,297 B1 * | 5/2001 | Linden et al. ................... 514/46 |
| 6,914,053 B2 * | 7/2005 | Cristalli .......................... 514/46 |
| 7,214,665 B2 * | 5/2007 | Linden et al. ................... 514/46 |

FOREIGN PATENT DOCUMENTS

| WO | WO 2005/105803 A2 | 11/2005 |
| WO | WO 2006/015357 A2 | 2/2006 |

OTHER PUBLICATIONS

International Search Report dated Aug. 31, 2010, an International Preliminary Report on Patentability and a Written Opinion of the International Searching Authoirty, dated Jan. 12, 2012; 9 pages.

* cited by examiner

*Primary Examiner* — Layla Bland

(57) ABSTRACT

Provided herein are alkoxy-carbonyl-amino-alkynyl-adenosine compounds and derivatives thereof and pharmaceutical compositions containing the same that are selective agonists of $A_{2A}$ adenosine receptors (ARs). These compounds and compositions are useful as pharmaceutical agents.

33 Claims, No Drawings

ALKOXY-CARBONYL-AMINO-ALKYNYL-ADENOSINE COMPOUNDS AND DERIVATIVES THEREOF AS $A_{2A}R$ AGONISTS

RELATED APPLICATIONS

This application claims priority to U.S. Provisional Application No. 61/221,692, filed on Jun. 30, 2009; the entire contents of which is incorporated herein by reference.

STATEMENT OF GOVERNMENT RIGHTS

This invention was made with the assistance of U.S. government support under United States Grant No. 1 R 41 AI 071496-01 from the National Institutes of Health (NIH). The U.S. government may have certain rights to the invention.

BACKGROUND OF THE INVENTION

Adenoside $A_{2A}$ receptors (also know as ADORA2A) are members of the G protein-coupled receptor (GPCR) family which possess seven transmembrane alpha helices. The receptor is mediated by G proteins, which activate adenylyl cyclase and is abundant in basal ganglia, vasculature and platelets and it is a major target of caffeine. The $A_{2A}$ receptor is responsible for regulating myocardial blood flow by vasodilating the coronary arteries, which increases blood flow to the myocardium, but may lead to hypotension. The $A_{2A}$ receptor is also expressed in the brain, where it has important roles in the regulation of glutamate and dopamine release. The $A_{2A}$ receptor signals in both the periphery and the CNS, with agonists explored as anti-inflammatory drugs and antagonists as useful in neurodegenerative disorders, such as Parkinson's disease.

There has been progressive development of compounds that are more and more potent and/or selective as agonists of $A_{2A}$ adenosine receptors (AR) based on radioligand binding assays and physiological responses. For example, U.S. Pat. Nos. 6,232,297 and 7,214,665 and U.S. Patent Application Publication Nos. 2006/004088, 2006/0217343, 2006/0040889 and 2007/0270373 all describe compounds having the general formula:

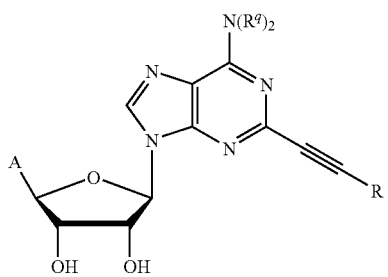

wherein R contains a ring. These compounds are reported to be $A_{2A}$ agonists.

U.S. Pat. No. 6,914,053 describes compounds of the following formula:

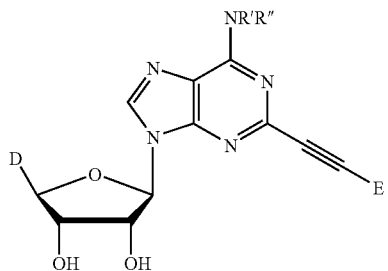

wherein E can be a variety of linear and cyclic groups and R" is an alkoxy or cycloalkoxy group. The compounds described therein are said to be $A_3$ agonists.

In U.S. Application Patent Publication No. 2006-0100169, International Application Publication Nos. WO 2006/015357 and WO 2006/101920 and Neuroscience, 141, 2029-2039 (2006), the compound 4-{3-[6-amino-9-((2R,3R,4S,5S)-5-cyclopropylcarbamoyl-3,4-dihydroxytetrahydrofuran-2-yl)-9H-purin-2-yl]-2-propynyl}-piperidine-1-carboxylic acid methyl ester, which is adenosine derivative, is disclosed and the compound is suggested to be useful as an anti-inflammatory agent, a coronary artery vasodilator, a neuroprotective agent or the like.

In International Application Publication No. WO 03/029264 and Neuroscience, 141, 2029-2039 (2006), the compounds 4-{3-[6-amino-9-((2R,3R,4S,5S)-5-ethylcarbamoyl-3,4-dihydroxytetrahydrofuran-2-yl)-9H-purin-2-yl]-2-propynyl}-piperidine-1-carboxylic acid methyl ester and 4-{3-[6-amino-9-((2R,3R,4S,5S)-5-ethylcarbamoyl-3,4-dihydroxytetrahydrofuran-2-yl)-9H-purin-2-yl]-2-propynyl}-piperidine-1-carboxylic acid isobutyl ester, both of which are adenosine derivatives, are disclosed, and in Japanese Patent Application Publication No. 2002-536300, the compound 4-{3-[6-amino-9-((2R,3R,4S,5S)-5-ethylcarbamoyl-3,4-dihydroxytetrahydrofuran-2-yl)-9H-purin-2-yl]-2-propynyl}-cyclohexane-1-carboxylic acid methyl ester, which is adenosine derivative, is disclosed. Further, in these documents, these compounds are suggested to be useful as anti-inflammatory agents.

Despite the increasing development of adenosine $A_{2A}$ receptor agonists, as described above, only one, regadenoson, has been approved for use in the United States as a coronary vasodilator. Typical issues involved with administration these compounds include side effects due to the wide distribution of adenosine receptors, low brain penetration (which is important for the targeting of CNS diseases), short half-life of compounds, or a lack of effects, in some cases possibly due to receptor desensitization or to low receptor density in the targeted tissue. Therefore, it is important to continue to synthesize and test additional $A_{2A}$ receptor agonists in order to develop new and improved therapeutic agents.

SUMMARY OF THE INVENTION

Accordingly, in one embodiment, the present invention provides, at least in part, adenosine $A_{2A}$ receptor agonsist (e.g., a compound of formula Ia, formula Ib, formula 1 or one or more of Table 1 or one or more of Table 2) and derivatives thereof or stereoisomers or pharmaceutically acceptable salts thereof.

In another embodiment, the present invention also provides, at least in part, pharmaceutical compositions comprising adenosine $A_{2A}$ receptor agonists (e.g., a compound of formula Ia, formula Ib, formula 1 or one or more of Table 1 or one or more of Table 2) or stereoisomer or a pharmaceutically acceptable salt thereof and a pharmaceutically acceptable excipient.

In yet another embodiment, the present invention also provides, at least in part, methods of treating a pathological condition or symptom in a mammal for which the $A_{2A}$ receptor is implicated (e.g., an adenosine $A_{2A}$ receptor associated state, such as glaucoma or ocular hypertension) and agonism of the receptor provides therapeutic benefit by administering to a subject an effective amount of an adenosine $A_{2A}$ receptor agonist (e.g., a compound of formula Ia, formula Ib, formula 1 or one or more of Table 1 or one or more of Table 2), or a pharmaceutically acceptable salt thereof.

In another embodiment, the present invention provides, at least in part, methods of treating and/or preventing an adenosine $A_{2A}$ receptor-associated state in a subject by administering to the subject an effective amount of an adenosine $A_{2A}$ receptor agonist (e.g., a compound of formula Ia, formula Ib, formula 1 or one or more of Table 1 or one or more of Table 2), or a pharmaceutically acceptable salt thereof.

Also provided are adenosine $A_{2A}$ receptor agonists (e.g., a compound of formula Ia, formula Ib, formula 1 or one or more of Table 1 or one or more of Table 2) for use in medical therapy.

Also provided herein is the use of adenosine $A_{2A}$ receptor agonists (e.g., a compound of formula Ia, formula Ib, formula 1 or one or one or more of Table 1 or one or more of Table 2) for the manufacture of a medicament for the treatment of a pathological condition or symptom in a mammal for which the $A_{2A}$ receptor is implicated (e.g., an adenosine $A_{2A}$ receptor associated state, such as glaucoma or ocular hypertension) and agonism of the receptor provides therapeutic benefit.

These and other aspects of the present invention have been accomplished in view of the discovery of the adenosine compounds and derivatives thereof described herein.

All embodiments described in this application are contemplated to be combinable with any other embodiment(s) where applicable, including embodiments specifically described under different aspects of the invention or in separate sections.

DETAILED DESCRIPTION OF THE INVENTION

The indefinite articles "a" and "an" mean "at least one" or "one or more" when used in this application, including the claims, unless specifically indicated otherwise.

1. Methods

In one embodiment, provided herein is a therapeutic method for treating a disease and/or condition in a mammal where the activity of $A_{2A}$ adenosine receptors is implicated (e.g., an adenosine $A_{2A}$ receptor associated state, such as glaucoma or ocular hypertension) and agonism of these receptors is desired, comprising administering to a mammal in need thereof a therapeutically effective amount of an adenosine $A_{2A}$ receptor agonist (e.g., a compound of formula Ia, formula Ib, formula 1 or one or more of Table 1 or one or more of Table 2), or a stereoisomer or pharmaceutically acceptable salt thereof.

The language "adenosine $A_{2A}$ receptor agonist" includes compounds that activate the adenosine $A_{2A}$ receptor with a $K_i$ of <1 µM as determined by the binding assay described herein (see Example II). An adenosine $A_{2A}$ receptor agonist may also be cross reactive with other adenosine receptor subtypes (e.g., $A_1$, $A_{2B}$, and $A_3$). In one embodiment, the adenosine $A_{2A}$ receptor agonist may be selective for an $A_{2A}$ receptor (e.g., at least a ratio of 10:1, 50:1, or 100:1 over another adenosine receptor subtype) or may activate/antagonize other receptors with a greater or lesser affinity than the $A_{2A}$ receptor. In other embodiments, the adenosine $A_{2A}$ receptor agonist is a compound of formula Ia, formula Ib, formula 1 or one or more of Table 1 or one or more of Table 2.

In another embodiment, provided herein is an adenosine $A_{2A}$ receptor agonist (e.g., a compound of formula Ia, formula Ib, formula 1 or one or more of Table 1 or one or more of Table 2) for use in medical therapy.

In another embodiment, provided herein is use of an adenosine $A_{2A}$ receptor agonist (e.g., a compound of formula Ia, formula Ib, formula 1 or one or more of Table 1 or one or more of Table 2) for the manufacture of a medicament for the treatment of an adenosine $A_{2A}$ receptor associated state such as glaucoma or ocular hypertension.

In some embodiments, provided herein is a method of treating an adenosine $A_{2A}$ receptor associated state in a subject by administering to the subject an effective amount of an adenosine $A_{2A}$ receptor agonist (e.g., a compound of formula Ia, formula Ib, formula 1 or one or more of Table 1 or one or more of Table 2) or a pharmaceutically acceptable salt thereof.

The language "treat" or "treating" includes the treatment of an adenosine $A_{2A}$ receptor associated state in a subject, and includes: (a) preventing the adenosine $A_{2A}$ receptor associated state from occurring in a subject; (b) inhibiting the adenosine $A_{2A}$ receptor associated state, e.g., arresting its development; and/or (c) relieving the adenosine $A_{2A}$ receptor associated state, e.g., causing regression of the adenosine $A_{2A}$ receptor associated state until a desired endpoint is reached. Treating also includes the amelioration of a symptom of an adenosine $A_{2A}$ receptor associated state (e.g., lessen the pain or discomfort), wherein such amelioration may or may not be directly affecting the disease (e.g., cause, transmission, expression, etc.).

The language "therapeutically effective amount" includes an amount of an adenosine $A_{2A}$ receptor agonist that is effective to treat, prevent or ameliorate an adenosine $A_{2A}$ receptor associated state in a subject when administered alone or in combination with another therapeutic agent. The language "therapeutically effective amount" also includes an amount of the combination of compounds claimed that is effective to treat the desired indication. The combination of compounds can be a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

The language "subject" includes one or more warm blooded mammals that are typically under medical care (e.g., mammals). Examples of subjects include, but are not limited to cats, dogs, monkeys, chimpanzees, rats, mice, cows, horses, pigs and humans. In one embodiment, the subject is at risk or is predisposed to an adenosine $A_{2A}$ receptor associated state. In another embodiment, the subject is suffering from an adenosine $A_{2A}$ receptor associated state.

The language "adenosine $A_{2A}$ receptor associated state" includes those diseases or disorders in which are directly or indirectly implicated in the adenosine $A_{2A}$ receptor pathway. Without being bound by theory, it is thought that administration of an adenosine $A_{2A}$ receptor agonist upregulates the biological activity of the adenosine $A_{2A}$ receptor by the binding of the agonist to the receptor, thereby activating the receptor and triggering the downstream biological pathway associated with the activity of the adenosine $A_{2A}$ receptor. Accordingly, an adenosine $A_{2A}$ receptor associated state includes those diseases and disorders directly associated with the inactivity or downregulation of the adenosine $A_{2A}$ receptor or the inactivity or downregulation of the biological pathway associated with the adenosine $A_{2A}$ receptor. Examples of adenosine $A_{2A}$ receptor associated states include inflammatory disorders and tissue activity, sickle cell disease, sepsis, septic shock, meningitis, peritonitis, arthritis, hemolytic uremic syndrome, glaucoma and ocular hypertension.

In another embodiment, provided herein is a method for preventing or treating glaucoma or ocular hypertension in a subject by administering to a subject in need thereof a therapeutically effective amount of an adenosine $A_{2A}$ receptor agonist (e.g., a compound of formula Ia, formula Ib, formula 1 or one or more of Table 1 or one or more of Table 2), or a stereoisomer or pharmaceutically acceptable salt thereof.

The term "glaucoma" includes a group of eye conditions that lead to damage to the optic nerve, the nerve that carries visual information from the eye to the brain. It is an intractable eye disease which exhibits increased intraocular pressure due to a variety of factors and involves a risk of leading to blindness. It is known that the incidence rate of glaucoma increases with age, and the progression of optic nerve injury also accelerates with age. In many cases, damage to the optic nerve is due to increased pressure in the eye, also known as intraocular pressure (IOP). Glaucoma includes open-angle glaucoma, which includes symptoms such as a gradual loss or peripheral vision (also called tunnel vision); angle-closure glaucoma, which includes symptoms such as sudden, severe pain in one eye, decreased or cloudy vision, nausea and vomiting, rainbow-like halos around lights, red and/or swollen eye, and congenital glaucoma, which includes symptoms that are usually noticed when the child is a few months old, such as cloudiness of the front of the eye, enlargement of one eye or both eyes, red eye and sensitivity to light.

The language "ocular hypertension" refers to the condition in which the intraocular pressure is higher than normal, in the absence of optic nerve damage or visual field loss. One of skill in the art would understand that normal intraocular pressure is between about 10 mmHg and 20 mmHg, where the average value of intraocular pressure is 15.5 mmHg with fluctuations of about 2.75 mmHg. The language "intraocular pressure" refers to the fluid pressure of the aqueous humor inside the eye.

In yet another embodiment, provided herein is a method of reducing interocular pressure in a subject comprising administering to the subject an effective amount of an adenosine $A_{2A}$ receptor agonist (e.g., a compound of formula Ia, formula Ib, formula 1 or one or more of Table 1 or one or more of Table 2). The language "reducing ocular hypertension" includes the decrease and/or the complete elimination of ocular hypertension. In one embodiment, the intraocular pressure is reduced by about 5%, by about 10%, by about 15%, by about 20%, by about 25%, by about 30%, by about 35%, by about 40%, by about 45%, by about 50%, by about 55%, by about 60%, by about 65%, by about 60%, by about 75%, by about 80%, by about 85%, by about 90%, by about 95% or by about 100% compared to the intraocular pressure prior to treatment.

In one embodiment, the inflammatory tissue activity, disorder or condition can be due to (a) pathological agents, (b) physical, chemical, or thermal trauma, or (c) the trauma of medical procedures, such as organ, tissue, or cell transplantation; angioplasty (PCTA); inflammation following ischemia/reperfusion; or, grafting. In yet another embodiment, the inflammatory disorder is includes allergen-induced inflammation, ischemia-reperfusion injury, sepsis and autoimmune diseases. Without being bound by theory, stressed or injured tissues release endogenous adenosine, which blocks potentially destructive inflammatory cascades by binding to $A_{2A}$ adenosine receptors and decreasing activation of platelets, leukocytes and endothelial cells. In these tissues, adenosine acts by reducing expression of adhesion molecules and release of pro-inflammatory mediators (e.g., reactive oxygen species, elastase and tumor necrosis factor-alpha).

Further examples of inflammatory tissue activity or inflammatory disorders include inflammation due to: (a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis; (b) allergic diseases such as asthma, hay fever, rhinitis, poison ivy, vernal conjunctivitis and other eosinophil-mediated conditions; (c) skin diseases such as psoriasis, contact dermatitis, eczema, infectious skin ulcers, healing of open wounds, cellulitis; (d) infectious diseases including sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), chronic obstructive pulmonary disease (COPD), lyme disease, HIV infection, (TNFα-enhanced HIV replication, TNFα inhibition of reverse transcriptase inhibitor activity); (e) wasting diseases: cachexia secondary to cancer and HIV; (f) organ, tissue or cell transplantation (e.g., bone marrow, cornea, kidney, lung, liver, heart, skin, pancreatic islets) including transplant rejection, and graft versus host disease; (g) adverse effects from drug therapy, including adverse effects from amphotericin B treatment, adverse effects from immunosuppressive therapy, e.g., interleukin-2 treatment, adverse effects from OKT3 treatment, contrast dyes, antibiotics, adverse effects from GM-CSF treatment, adverse effects of cyclosporine treatment, and adverse effects of aminoglycoside treatment, stomatitis and mucositis due to immunosuppression; (h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes; (i) dialysis, including pericarditis, due to peritoneal dialysis; (j) gout; and (k) chemical or thermal trauma due to burns, acid, alkali and the like.

Additional diseases include, for example, equine disorders such as laminitis and founder's disease.

In another embodiment, provided herein is a method of treating an inflammatory disorder, tissue activity or condition, comprising: administering at least one adenosine $A_{2A}$ receptor agonist (e.g., a compound of formula Ia, formula Ib, formula 1 or one or more of Table 1 or one or more of Table 2) in combination with at least one other anti-inflammatory compound (e.g., a Type IV PDE inhibitor).

In another embodiment, provided herein is a method for treating neuropathic pain, comprising: intrathecally administering to a patient in need thereof a therapeutically effective amount of an adenosine $A_{2A}$ receptor agonist (e.g., a compound of formula Ia, formula Ib, formula 1 or one or more of Table 1 or one or more of Table 2) or a pharmaceutically acceptable salt thereof.

In another embodiment, the present invention provides a method for treating biological diseases, comprising: administering a therapeutically effective amount of an anti-pathogenic agent (e.g., an antibiotic, antifungal, or antiviral agent) in combination with an adenosine $A_{2A}$ receptor agonist. If no anti-pathogenic agent is known the adenosine $A_{2A}$ receptor agonist can be used alone to reduce inflammation, as may occur during infection with antibiotic resistant bacteria or certain viruses (e.g., those that cause SARS, influenze, or Ebola). Optionally, the method further comprises administration of a type IV PDE inhibitor. The adenosine $A_{2A}$ receptor agonist can provide adjunctive therapy for treatment conditions such as, the inflammation, caused by sepsis, for example, human uremic syndrome when administered with antibiotics in the treatment of bio-terrorism weapons, such as anthrax, tularemia, *Escherichia coli*, lymes disease, and plague. The adenosine $A_{2A}$ receptor agonists (e.g., a compound of formula Ia, formula Ib, formula 1 or one or more of Table 1 or one or more of Table 2) can also provide adjunctive therapy for treatment of lethal pathogenic infections (e.g., bacterial, fungal, or viral) (e.g., anthrax, tularemia, *Escherichia coli*, and plague), comprising: administering an anti-pathognic agent in combination with a compound described herein. Also included are yeast and fungal infections with or without anti-yeast or anti-fungal agents.

In one embodiment, provided herein is a method for treating a pathological condition or symptom in a subject, wherein the activity of adenosine $A_{2A}$ receptors is implicated and agonism of such activity is desired (e.g., an adenosine $A_{2A}$ receptor associated state), comprising administering to the subject an effective amount of an adenosine $A_{2A}$ receptor agonist (e.g., a compound of formula Ia, formula Ib, formula 1 or one or more of Table 1 or one or more of Table 2).

In one embodiment, the pathological condition or symptom is caused by autoimmune stimulation, inflammation, allergic diseases, skin diseases, infectious diseases, wasting diseases, organ transplantation, tissue or cell transplantation, open wounds, adverse effects from drug therapy, a cardiovascular condition, ischemia-reperfusion injury, dialysis, gout, chemical trauma, thermal trauma, diabetic nephropathy, sickle cell disease, laminitis, founder's disease, glaucoma, and ocular hypertension.

In another embodiment, provided herein is a method to diagnose myocardial perfusion abnormalities in a subject comprising: (a) parenterally administering to said subject an adenosine $A_{2A}$ receptor agonist (e.g., a compound of formula Ia, formula Ib, formula 1 or one or more of Table 1 or one or more of Table 2); and (b) performing a technique on said subject to detect the presence of coronary artery stenoses, assess the severity of coronary artery stenoses or both.

The compounds provided herein can be used as a pharmacologic vasodilator agent that can be used with clinical perfusion imaging techniques, for example, for diagnosing and assessing the extent of coronary artery disease. Imaging techniques include planar or single photon emission computed tomography (SPECT), gamma camera scintigraphy, positron emission tomography (PET), nuclear magnetic resonance (NMR) imaging, magnetic resonance imaging (MRI) imaging, perfusion contrast echocardiography, digital subtraction angiography (DSA), and ultrafast X-ray computed tomography (CINE CT).

The compounds and compositions provided herein can be administered as pharmacological stressors and used in conjunction with any one of several noninvasive diagnostic procedures to measure aspects of myocardial, coronary, and/or ventricular perfusion. Thus, provided herein is a method for perfusion imaging in a subject, such as a human, comprising (1) administering an amount of an adenosine $A_{2A}$ receptor agonist (e.g., a compound of formula Ia, formula Ib, formula 1 or one or more of Table 1 or one or more of Table 2) to the subject, and (2) performing a technique on said subject to detect and/or determine the presence of an abnormality. Aspects that can be measured include coronary artery stenoses, myocardial dysfunction (e.g., myocardial ischemia, coronary artery disease, ventricular dysfunction, and differences in blood flow through disease-free coronary vessels and/or stenotic coronary vessels), myocardial contractile dysfunction, the presence of regional wall motion abnormalities, the functional significance of stenotic coronary vessels, coronary artery disease, ischemic ventricular dysfunction, and vasodilatory capacity (reserve capacity) of coronary arteries in humans. Radiopharmaceuticals are typically used in diagnostic methods. The radiopharmaceutical agent may comprise, for example, a radionuclide selected from the group consisting of thallium-201, technetium-99m, nitrogen-13, rubidium-82, iodine-123 and oxygen-15.

The diagnostic methods provided typically involve the administration of one or more adenosine $A_{2A}$ receptor agonists (e.g., a compound of formula Ia, formula Ib, formula 1 or one or more of Table 1 or one or more of Table 2) by intravenous infusion in doses which are effective to provide coronary artery dilation (approximately 0.25-500 or 1-250 mcg/kg/min). However, its use in the invasive setting may involve the intracoronary administration of the drug in bolus doses of 0.5-50 mcg.

2. Compounds

In one embodiment, the adenosine $A_{2A}$ receptor agonist is a compound of formula Ia:

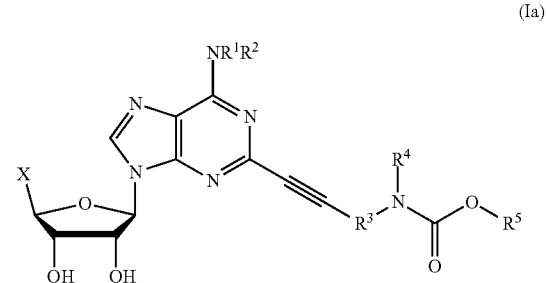

(Ia)

wherein:

$R^1$ and $R^2$ independently are selected from: H, $C_{1-8}$ alkyl, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{5-10}$ aryl, ($C_{5-10}$ aryl)$C_{1-8}$ alkyl-, $C_{5-10}$ heteroaryl, and ($C_{5-10}$ heteroaryl)$C_{1-8}$ alkyl-;

$R^3$ is —$C_{1-8}$ alkyl-;

$R^4$ is independently selected from: H, —$C_{2-6}$ alkyl-$OR^a$, —$C_{2-6}$ alkyl-$NR^aR^b$, $C_{1-10}$ alkyl, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;

$R^5$ is selected from: $C_{1-8}$ alkyl, —$C_{2-6}$ alkyl-$NR^aR^b$, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, —$C_{2-6}$ alkyl-$OR^a$ and ($C_{5-10}$ heteroaryl)$C_{1-8}$ alkyl-;

X is selected from: —CH$_2$OR$^c$, —OCO$_2$R$^c$, —OCH$_2$OC(O)R$^c$, —C(O)NR$^c$R$^d$, —CH$_2$SR$^c$, —C(S)OR$^c$, —CH$_2$OC(S)R$^c$, C(S)NR$^c$R$^d$ and —CH$_2$NR$^c$R$^d$; or X is a C$_{5-6}$ heteroaryl;

R$^a$ and R$^b$ are each independently selected from H, C$_{1-8}$ alkyl, (C$_{1-8}$ alkoxy)$_{1-3}$C$_{1-8}$ alkyl-, C$_{3-8}$ cycloalkyl, (C$_{3-8}$ cycloalkyl)C$_{1-8}$ alkyl-, C$_{6-10}$ aryl, (C$_{6-10}$ aryl)C$_{1-8}$ alkyl-, C$_{5-10}$ heteroaryl, and (C$_{5-10}$ heteroaryl)C$_{1-8}$ alkyl-; or R$^a$ and R$^b$, together with the nitrogen to which they are attached, form a ring selected from pyrrolidino, piperidino, morpholino, and thiomorpholino ring;

R$^c$ is selected from: H, C$_{1-8}$ alkyl, C$_{3-6}$ cycloalkyl, and (C$_{3-6}$ cycloalkyl)C$_{1-8}$ alkyl-; and R$^d$ is selected from: H, C$_{1-8}$ alkyl, (C$_{1-8}$ alkoxy)$_{1-3}$C$_{1-8}$ alkyl-, C$_{3-8}$ cycloalkyl, C$_{6-10}$ aryl, (C$_{6-10}$ aryl)C$_{1-8}$ alkyl-, C$_{5-10}$ heteroaryl, and (C$_{5-10}$ heteroaryl)C$_{1-8}$ alkyl-; and stereoisomers or pharmaceutically acceptable salts thereof.

In one embodiment, when R$^1$ or R$^2$ are not H, R$^1$ and R$^2$ are independently substituted with 0-3 groups selected from F, Cl, Br, I, —CN, OH, OC$_{1-4}$ alkyl, CF$_3$, and OCF$_3$;

In another embodiment, R$^3$ is substituted with 0-2 groups selected from C$_{1-10}$ alkyl, C$_{3-8}$ cycloalkyl, C$_{1-10}$ alkoxy, C$_{3-8}$ cyclic alkoxy, F, Cl, Br, I, —CN, OH, OC$_{1-4}$ alkyl, CF$_3$, and OCF$_3$.

In one embodiment, R$^3$ is interrupted by 0-1 groups selected from: O and NR$^a$.

In yet another embodiment, when R$^4$ is not hydrogen, R$^4$ is substituted with 0-2 R$^{4a}$, wherein R$^{4a}$ is independently selected from F, Cl, Br, I, —CN, OH, OC$_{1-4}$ alkyl, CF$_3$, OCF$_3$, CO$_2$R$^a$, and C(O)NR$^a$R$^b$.

In a further embodiment, R$^5$ is substituted with 0-3 R$^{5a}$, wherein each R$^{5a}$ is independently selected from C$_{1-8}$ alkyl, F, Cl, Br, I, —CN, OR$^a$, SR$^a$, NR$^a$R$^b$, CF$_3$, OCF$_3$, COR$^a$, CO$_2$R$^a$, C(O)NR$^a$R$^b$, OC(O)R$^a$, OCO$_2$R$^a$, OC(O)NR$^a$R$^b$, NR$^b$COR$^a$, NR$^b$CO$_2$R$^a$, NR$^b$C(O)NR$^a$R$^b$, S(O)$_p$NR$^a$R$^b$, C$_{3-10}$ cycloalkyl, (C$_{3-10}$ cycloalkyl)C$_{1-8}$ alkyl-, C$_{4-10}$ heterocycle, (C$_{4-40}$ heterocycle)C$_{1-8}$ alkyl-, C$_{6-10}$ aryl, C$_{6-10}$ aryloxy, (C$_{6-10}$ aryl)C$_{1-8}$ alkyl-, C$_{5-10}$ heteroaryl, and (C$_{5-40}$ heteroaryl)C$_{1-8}$ alkyl- and p is independently selected from: 0, 1, and 2.

In one embodiments, R$^5$ is C$_{6-10}$ aryl (e.g., phenyl) optionally substituted with 0-5 R$^{5a}$ groups selected from C$_{1-10}$ alkoxy, C$_{3-8}$ cyclic alkoxy, halo-C$_{1-10}$ alkyl, nitro, cyano, C$_{1-8}$ alkyl, —NO$_2$, F, Cl, Br, I, —CN, OR$^a$, SR$^a$, NR$^a$R$^b$, CF$_3$, OCF$_3$, COR$^a$, CO$_2$R$^a$, C(O)NR$^a$R$^b$, OC(O)R$^a$, OCO$_2$R$^a$, OC(O)NR$^a$R$^b$, NR$^b$COR$^a$, NR$^b$CO$_2$R$^a$, NR$^b$C(O)NR$^a$R$^b$, S(O)$_p$NR$^a$R$^b$, C$_{3-10}$ cycloalkyl, (C$_{3-10}$ cycloalkyl)C$_{1-8}$ alkyl-, C$_{4-10}$ heterocycle, (C$_{4-10}$ heterocycle)C$_{1-8}$ alkyl-, C$_{6-10}$ aryl, C$_{6-10}$ aryloxy, (C$_{6-10}$ aryl)C$_{1-8}$ alkyl-, C$_{5-10}$ heteroaryl, and (C$_{5-10}$ heteroaryl)C$_{1-8}$ alkyl- and p is independently selected from: 0, 1, and 2.

In yet another embodiment, each alkyl of R$^5$ is interrupted by 0-2 groups selected from: C(=O), O, S, C(O)NR$^a$, NR$^a$C(O), and NR$^a$.

In another embodiment, X is a C$_{5-6}$ heteroaryl optionally substituted with 0-2 groups selected from C$_{1-8}$ alkyl, C$_{2-8}$ alkenyl, C$_{3-8}$ cycloalkyl, (C$_{3-8}$ cycloalkyl)C$_{1-8}$ alkyl-, C$_{3-8}$ cycloalkenyl, (C$_{3-8}$ cycloalkenyl)C$_{1-8}$ alkyl-, C$_{6-40}$ aryl, (C$_{6-10}$ aryl)C$_{1-8}$ alkyl-, C$_{5-10}$ heteroaryl, and (C$_{5-10}$ heteroaryl)C$_{1-8}$ alkyl-, wherein each alkyl or alkenyl group is optionally interrupted by 0-2 groups selected from: O, S, and N(R$^a$).

In another embodiment, provided herein is a compound of formula Ia or a stereoisomer or pharmaceutically acceptable salt thereof, wherein:
R$^1$ and R$^2$ independently are selected from: H, C$_{1-4}$ alkyl, C$_{3-6}$ cycloalkyl, and (C$_{3-6}$ cycloalkyl)C$_{1-2}$ alkyl-;
R$^3$ is —C$_{1-4}$ alkyl-optionally substituted with 0-1 groups selected from F, Cl, OH, OC$_{1-2}$ alkyl, CF$_3$, and OCF$_3$; and, R$^4$ is selected from: H, —C$_{2-4}$ alkyl-OR$^a$, —C$_{2-4}$ alkyl-NR$^a$R$^b$, C$_{1-6}$ alkyl, C$_{3-6}$ cycloalkyl, (C$_{3-6}$ cycloalkyl)C$_{1-4}$ alkyl-, phenyl, (phenyl)C$_{1-4}$ alkyl-, C$_{5-6}$ heteroaryl, and (C$_{5-6}$ heteroaryl)C$_{1-4}$ alkyl-, wherein R$^4$ group is optionally substituted with 0-2 R$^{4a}$ when R$^4$ is not hydrogen; and,
R$^{4a}$ is independently selected from F, Cl, —CN, OH, OC$_{1-4}$ alkyl, CF$_3$, OCF$_3$, CO$_2$R$^a$, and C(O)NR$^a$R$^b$.

In another embodiment, provided herein is a compound of formula Ia or a stereoisomer or pharmaceutically acceptable salt thereof, wherein:
R$^1$ and R$^2$ are H;
R$^3$ is —CH$_2$—; and,
R$^4$ is selected from: H and CH$_3$.

In another embodiment, provided herein is a compound of formula Ia or a stereoisomer or pharmaceutically acceptable salt thereof, wherein:
X is selected from: —CH$_2$OR$^c$ and —C(O)NR$^c$R$^d$; or X is a C$_{5-6}$ heteroaryl, optionally substituted with 0-1 groups selected C$_{1-4}$ alkyl, C$_{3-6}$ cycloalkyl, (C$_{3-6}$ cycloalkyl)CH$_2$—, phenyl, and benzyl;
R$^c$ is selected from: H, methyl, ethyl, cyclopropyl and cyclobutyl; and,
R$^d$ is selected from: H and C$_{1-4}$ alkyl.

In another embodiment, provided herein is a compound of formula Ia or a stereoisomer or pharmaceutically acceptable salt thereof, wherein:
X is selected from: —CH$_2$OR$^c$ and —C(O)NR$^c$R$^d$;
R$^c$ is selected from: methyl, ethyl, cyclopropyl and cyclobutyl; and,
R$^d$ is selected from: H and CH$_3$.

In another embodiment, provided herein is a compound of formula Ia or a stereoisomer or pharmaceutically acceptable salt thereof, wherein:
R$^5$ is selected from: C$_{1-6}$ alkyl, —C$_{2-6}$ alkyl-NR$^a$R$^b$, C$_{3-6}$ cycloalkyl, (C$_{3-8}$ cycloalkyl)C$_{1-6}$ alkyl-, C$_{4-10}$ heterocycle, (C$_{4-10}$ heterocycle)C$_{1-6}$ alkyl-, C$_{6-10}$ aryl, (C$_{6-10}$ aryl)C$_{1-6}$ alkyl-, C$_{5-10}$ heteroaryl, —C$_{2-6}$ alkyl-OR$^a$ and (C$_{5-10}$ heteroaryl)C$_{1-6}$ alkyl-, wherein each R$^5$ group is optionally substituted with 0-2 R$^{5a}$ and each alkyl of R$^5$ is optionally interrupted by 0-2 groups selected from: C(=O), O, S, C(O)NR$^a$, NR$^a$C(O), and NR$^a$;
R$^{5a}$ is independently selected from C$_{1-4}$ alkyl, F, Cl, —CN, OR$^a$, SR$^a$, NR$^a$R$^b$, CF$_3$, OCF$_3$, COR$^a$, CO$_2$R$^a$, C(O)NR$^a$R$^b$, OC(O)R$^a$, NR$^b$COR$^a$, S(O)$_p$NR$^a$R$^b$, C$_{3-6}$ cycloalkyl, (C$_{3-6}$ cycloalkyl)C$_{1-2}$ alkyl-, C$_{5-6}$ heterocycle, (C$_{5-6}$ heterocycle)C$_{1-2}$ alkyl-, C$_{6-10}$ aryl, C$_{6-10}$ aryloxy, (C$_{6-10}$ aryl)C$_{1-2}$ alkyl-, C$_{5-6}$ heteroaryl, and (C$_{5-6}$ heteroaryl)C$_{1-2}$ alkyl-;
R$^a$ and R$^b$ are each independently selected from H, C$_{1-4}$ alkyl, (C$_{1-6}$ alkoxy)C$_{1-4}$ alkyl-, C$_{3-6}$ cycloalkyl, (C$_{3-6}$ cycloalkyl)C$_{1-2}$ alkyl-, phenyl, (phenyl)C$_{1-2}$ alkyl-, C$_{5-6}$ heteroaryl, and (C$_{5-6}$ heteroaryl)C$_{1-2}$ alkyl-; or R$^a$ and R$^b$, together with the nitrogen to which they are attached, form a ring selected from pyrrolidino, piperidino, morpholino, and thiomorpholino ring.

In another embodiment, provided herein is a compound of formula Ia or a stereoisomer or pharmaceutically acceptable salt thereof, wherein:
R$^5$ is selected from: C$_{1-6}$ alkyl, —C$_{2-6}$ alkyl-NR$^a$R$^b$, C$_{3-6}$ cycloalkyl, (C$_{3-8}$ cycloalkyl)C$_{1-8}$ alkyl-, C$_{5-6}$ heterocycle, (C$_{5-6}$ heterocycle)C$_{1-6}$ alkyl-, phenyl, (phenyl)C$_{1-6}$ alkyl-, C$_{5-6}$ heteroaryl, —C$_{2-6}$ alkyl-OR$^a$, and (C$_{5-6}$ heteroaryl)C$_{1-6}$ alkyl-, wherein each R$^5$ group is optionally substituted with 0-2 R$^{5a}$ and each alkyl of R$^5$ is optionally interrupted by 0-2 groups selected from: C(=O), O, C(O)NR$^a$, NR$^a$C(O), and NR$^a$;
R$^{5a}$ is independently selected from C$_{1-4}$ alkyl, F, Cl, OR$^a$, CF$_3$, OCF$_3$, COR$^a$, C(O)NR$^a$R$^b$, C$_{3-6}$ cycloalkyl, (C$_{3-6}$ cycloalkyl)CH$_2$—, phenyl, and benzyl;
R$^a$ and R$^b$ are each independently selected from H, C$_{1-4}$ alkyl, (C$_{1-4}$ alkoxy)C$_{1-4}$ alkyl-, C$_{3-6}$ cycloalkyl, (C$_{3-6}$ cycloalkyl)CH$_2$—, phenyl, and benzyl; or R$^a$ and R$^b$, together with the nitrogen to which they are attached, form a ring selected from pyrrolidino, piperidino, and morpholino.

In one embodiment, R$^1$ and R$^2$ are each hydrogen; R$^3$ is C$_1$ alkyl (e.g., methylene); X is —C(O)NR$^c$R$^d$; R$^c$ is hydrogen; R$^d$ is C$_{1-8}$ alkyl, for example, C$_2$ alkyl (e.g., ethyl); R$^4$ is C$_{1-10}$ alkyl, for example, C$_1$ alkyl (e.g., methyl) and R$^5$ is C$_{1-8}$ alkyl, for example, C$_1$ alkyl (e.g., methyl).

In another embodiment, R$^1$ and R$^2$ are each hydrogen; R$^3$ is C$_1$ alkyl (e.g., methylene); X is —C(O)NR$^c$R$^d$; R$^c$ is hydrogen; R$^d$ is C$_{3-8}$ cycloalkyl, for example, C$_3$ cycloalkyl (e.g., cyclopropyl); R$^5$ is C$_{1-8}$ alkyl, for example, C$_1$ alkyl (e.g., methyl); and R$^4$ is C$_{3-8}$ cycloalkyl, for example, C$_3$ cycloalkyl (e.g., cyclopropyl), C$_4$ cycloalkyl (e.g., cyclobutyl) or C$_5$ cycloalkyl (e.g., cyclopentyl); and R$^4$ is C$_{1-10}$ alkyl, for example, C$_1$ alkyl (e.g., a optionally substituted methyl, for example, substituted with aryl, such as phenyl or cycloalkyl, such as cyclopropyl), C$_2$ alkyl (e.g., optionally substituted ethyl, for example, substituted with alkoxy, such as methoxy) C$_3$ alkyl (e.g., optionally substituted n-propyl or isopropyl, for example, substituted with alkoxy, such as methoxy or ethoxy), or C$_4$ alkyl (e.g., isobutyl).

In another embodiment, R$^1$ and R$^2$ are each hydrogen; R$^3$ is C$_1$ alkyl (e.g., methylene); X is —C(O)NR$^c$R$^d$; R$^c$ is hydrogen; R$^d$ is C$_{3-8}$ cycloalkyl, for example, C$_3$ cycloalkyl (e.g., cyclopropyl); R$^5$ is C$_{1-8}$ alkyl, for example, C$_1$ alkyl (e.g., methyl); R$^4$ is (C$_{3-8}$ cycloalkyl)C$_{1-8}$ alkyl- in which the cycloalkyl is a C$_3$ cycloalkyl (e.g., cyclopropyl) and said alkyl is a C$_1$ alkyl (e.g., methyl).

In another embodiment, R$^1$ and R$^2$ are each hydrogen; R$^3$ is C$_1$ alkyl (e.g., methylene); X is —C(O)NR$^c$R$^d$; R$^c$ is hydrogen; R$^d$ is C$_{3-8}$ cycloalkyl, for example, C$_3$ cycloalkyl (e.g., cyclopropyl); R$^5$ is C$_{1-8}$ alkyl, for example, C$_1$ alkyl (e.g., methyl); R$^4$ is (C$_{6-10}$ aryl)C$_{1-8}$ alkyl- in which the aryl is C$_6$ aryl (e.g., phenyl) and said alkyl is C$_1$ alkyl (e.g., methyl).

In another embodiment, R$^1$ and R$^2$ are each hydrogen; R$^3$ is C$_1$ alkyl (e.g., methylene); X is —C(O)NR$^c$R$^d$; R$^c$ is hydrogen; R$^d$ is C$_{3-8}$ cycloalkyl, for example, C$_3$ cycloalkyl (e.g., cyclopropyl); R$^4$ is C$_{1-10}$ alkyl, for example, C$_1$ alkyl (e.g., methyl); R$^5$ is C$_{6-10}$ aryl, for example, optionally substituted phenyl (e.g., halogen substituted phenyl, such as 4-fluorophenyl).

In another embodiment, R$^1$ and R$^2$ are each hydrogen; R$^3$ is C$_1$ alkyl (e.g., methylene); X is —C(O)NR$^c$R$^d$; R$^c$ is hydrogen; R$^d$ is C$_{3-8}$ cycloalkyl, for example, C$_3$ cycloalkyl (e.g., cyclopropyl); R$^4$ is C$_{1-10}$ alkyl, for example, C$_1$ alkyl (e.g., methyl); R$^5$ is —C$_{2-6}$ alkyl-OR$^a$ in which said alkyl is C$_2$ alkyl (e.g., ethyl) and R$^a$ is (C$_{6-10}$ aryl)C$_{1-8}$ alkyl- in which the aryl is C$_6$ aryl (e.g., phenyl) and said alkyl is C$_1$ alkyl (e.g., methyl).

In one embodiment, the compound of formula Ia is a compound of formula 1:

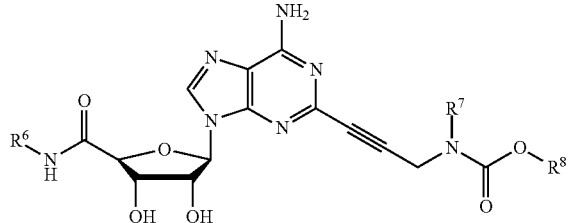

(1)

wherein

R$^6$ represents a hydrogen atom, an alkyl group, or a cycloalkyl group;

R$^7$ represents a hydrogen atom, a cycloalkyl group or an alkyl group;

R$^8$ represents an alkyl group, a cycloalkyl group, a phenyl group or a phenyl group substituted with at least a halogen atom or -G-O—R$^9$;

R$^9$ represents an alkyl group, a cycloalkyl group, a phenyl group, a (cycloalkyl)alkyl group, or a (phenyl)alkyl group; and G represents an alkylene group, and pharmaceutically acceptable salts thereof.

In some embodiment, in the compound of formula 1, (a1) R$^6$ represents an alkyl group, or a cycloalkyl group; and/or (a2) R$^7$ represents an alkyl group; and/or (a3) R$^8$ represents an alkyl group, a phenyl group, a phenyl group substituted with at least a halogen atom or -G-O—R$^9$; and/or (a4) R$^9$ represents a (phenyl)alkyl group; and/or G represents an alkylene group.

In some other embodiment, in the compounds represented by the general formula (1), examples include compounds that comprise one or each combination of two or more selected from the above (a1), (a2), (a3), (a4) and (a5), and salts thereof.

In yet other embodiments, in the compound of formula 1:

(b1) R$^6$ represents an ethyl group or a cyclopropyl group;

(b2) R$^7$ represents a methyl group;

(b3) R$^8$ represents a methyl group, a phenyl group, a 4-fluorophenyl group or -G-O—R$^9$;

(b4) R$^9$ represents a benzyl group; and, (b5) G represents an ethylene group.

In some embodiments, in the compounds represented by the general formula (1), examples include compounds that comprise one or each combination of two or more selected from the above (b1), (b2), (b3), (b4) and (b5), and salts thereof.

In one embodiment, R$^6$ is a cycloalkyl (e.g., cyclopropyl); R$^7$ is alkyl (e.g., methyl) and R$^8$ is alkyl (e.g., methyl).

In another embodiment, R$^6$ is alkyl (e.g., ethyl); R$^7$ is alkyl (e.g., methyl) and R$^8$ is alkyl (e.g., methyl).

In another embodiment, R$^6$ is cycloalkyl (e.g., cyclopropyl); R$^7$ is alkyl (e.g., ethyl, n-propyl, isopropyl, isobutyl, methoxyethyl, methoxypropyl, ethoxypropyl, cyclopropylmethyl or benzyl) and R$^8$ is alkyl (e.g., methyl).

In another embodiment, R$^6$ is cycloalkyl (e.g., cyclopropyl); R$^7$ is cycloalkyl (e.g., cyclopropyl, cyclobutyl or cyclopenyl) and R$^8$ is alkyl (e.g., methyl).

In another embodiment, R$^6$ is cycloalkyl (e.g., cyclopropyl), R$^7$ is alkyl (e.g., methyl) and R$^8$ is a phenyl group or a phenyl group substituted with at least a halogen atom (e.g., a fluorine at, for example, the 4-position of the phenyl).

In another embodiment, R$^6$ is cycloalkyl (e.g., cyclopropyl), R$^7$ is alkyl (e.g., methyl); R$^8$ is G-O—R$^9$; G is alkylene (e.g., ethylene) and R$^9$ is benzyl).

In other embodiments, the compounds of formula Ia and/or 1 include, for example, N-Cyclopropyl 2-{3-[methoxycarbonyl(methyl)amino]propyn-1-yl}adenosin-5'-uronamide;

N-Cyclopropyl 2-{3-[phenoxycarbonyl(methyl)amino]propyn-1-yl}adenosin-5'-uronamide;

N-Cyclopropyl 2-{3-[2-((benzyloxy)ethoxycarbonyl) (methyl)amino]propyn-1-yl}adenosin-5'-uronamide;

N-Cyclopropyl 2-{3-[4-fluorophenoxycarbonyl(methyl) amino]propyn-1-yl}adenosin-5'-uronamide; or N-Ethyl 2-{3-[methoxycarbonyl(methyl)amino]propyn-1-yl}adenosin-5'-uronamide.

In one embodiment, the adenosine $A_{2A}$ receptor agonist is a compound of formula Ib:

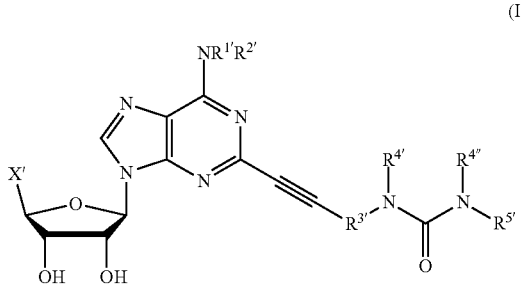

wherein:

$R^{1'}$ and $R^{2'}$ independently are selected from: H, $C_{1-8}$ alkyl, $C_{3-8}$ cycloalkyl, $(C_{3-8}$ cycloalkyl)$C_{1-8}$ alkyl-, $C_{4-10}$ heterocycle, $(C_{4-10}$ heterocycle)$C_{1-8}$ alkyl-, $C_{6-10}$ aryl, $(C_{6-10}$ aryl)$C_{1-8}$ alkyl-, $C_{5-10}$ heteroaryl, and $(C_{5-10}$ heteroaryl)$C_{1-8}$ alkyl-;

$R^{3'}$ is —$C_{1-8}$ alkyl-;

$R^{4'}$ and $R^{4''}$ are independently selected from: H, —$C_{2-6}$ alkyl-$OR^{a'}$, —$C_{2-6}$ alkyl-$NR^{a'}R^{b'}$, $C_{1-10}$ alkyl, $C_{3-8}$ cycloalkyl, $(C_{3-8}$ cycloalkyl)$C_{1-8}$ alkyl-, $C_{6-10}$ aryl, $(C_{6-10}$ aryl)$C_{1-8}$ alkyl-, $C_{5-10}$ heteroaryl, and $(C_{5-10}$ heteroaryl)$C_{1-8}$ alkyl-;

$R^{5'}$ is selected from: $C_{1-8}$ alkyl, —$C_{2-6}$ alkyl-$NR^{a}R^{b}$, $C_{3-8}$ cycloalkyl, $(C_{3-8}$ cycloalkyl)$C_{1-8}$ alkyl-, $C_{4-10}$ heterocycle, $(C_{4-10}$ heterocycle)$C_{1-8}$ alkyl-, $C_{6-10}$ aryl, $(C_{6-10}$ aryl)$C_{1-8}$ alkyl-, $C_{5-10}$ heteroaryl, —$C_{2-6}$ alkyl-$OR^{a}$ and $(C_{5-10}$ heteroaryl)$C_{1-8}$ alkyl-;

X' is selected from: —$CH_2OR^{c'}$, —$OCO_2R^{c'}$, —$OCH_2OC(O)R^{c'}$, —$C(O)NR^{c'}R^{d'}$, —$CH_2SR^{c'}$, —$C(S)OR^{c'}$, —$CH_2OC(S)R^{c'}$, $C(S)NR^{c'}R^{d'}$ and —$CH_2NR^{c'}R^{d'}$; or X' is a $C_{5-6}$ heteroaryl;

$R^{a'}$ and $R^{b'}$ are each independently selected from H, $C_{1-8}$ alkyl, $(C_{1-8}$ alkoxy)$_{1-3}C_{1-8}$ alkyl-, $C_{3-8}$ cycloalkyl, $(C_{3-8}$ cycloalkyl)$C_{1-8}$ alkyl-, $C_{6-10}$ aryl, $(C_{6-10}$ aryl)$C_{1-8}$ alkyl-, $C_{5-10}$ heteroaryl, and $(C_{5-10}$ heteroaryl)$C_{1-8}$ alkyl-; or $R^{a'}$ and $R^{b'}$, together with the nitrogen to which they are attached, form a ring selected from pyrrolidino, piperidino, morpholino and thiomorpholino ring;

$R^{c'}$ is selected from: H, $C_{1-8}$ alkyl, $C_{3-6}$ cycloalkyl, and $(C_{3-6}$ cycloalkyl)$C_{1-8}$ alkyl-; and $R^{d'}$ is selected from: H, $C_{1-8}$ alkyl, $(C_{1-8}$ alkoxy)$_{1-3}C_{1-8}$ alkyl-, $C_{3-8}$ cycloalkyl, $C_{6-10}$ aryl, $(C_{6-10}$ aryl)$C_{1-8}$ alkyl-, $C_{5-10}$ heteroaryl, and $(C_{5-10}$ heteroaryl)$C_{1-8}$ alkyl-; and stereoisomers or pharmaceutically acceptable salts thereof.

In one embodiment, $R^{1'}$ and $R^{2'}$ are independently substituted with 0-3 groups selected from F, Cl, Br, I, —CN, OH, $OC_{1-4}$ alkyl, $CF_3$, and $OCF_3$ when $R^{1'}$ and $R^{2'}$ are not hydrogen;

In another embodiment, $R^{3'}$ is substituted with 0-2 groups selected from $C_{1-10}$ alkyl, $C_{3-8}$ cycloalkyl, $C_{1-10}$ alkoxy, $C_{3-8}$ cyclic alkoxy, F, Cl, Br, I, —CN, OH, $OC_{1-4}$ alkyl, $CF_3$, and $OCF_3$.

In one embodiment, $R^{3'}$ is interrupted by 0-1 groups selected from: O and $NR^{a'}$.

In yet another embodiment, each $R^{4'}$ and $R^{4''}$ group is substituted with 0-2 $R^{a'}$, wherein $R^{4a'}$ is independently selected from F, Cl, Br, I, —CN, OH, $OC_{1-4}$ alkyl, $CF_3$, $OCF_3$, $CO_2R^a$, and $C(O)NR^aR^b$ when $R^{4'}$ and $R^{4''}$ are not hydrogen.

In a further embodiment, each $R^{5'}$ group is substituted with 0-3 $R^{5a'}$, wherein each $R^{5a'}$ is independently selected from $C_{1-8}$ alkyl, F, Cl, Br, I, —CN, $OR^{a'}$, $SR^{a'}$, $NR^{a'}R^{b'}$, $CF_3$, $OCF_3$, $COR^{a'}$, $CO_2R^{a'}$, $C(O)NR^{a'}R^{b'}$, $OC(O)R^{a'}$, $OCO_2R^{a'}$, $OC(O)NR^{a'}R^{b'}$, $NR^{b'}COR^{a'}$, $NR^{b'}CO_2R^{a'}$, $NR^{b'}C(O)NR^{a'}R^{b'}$, $S(O)_qNR^{a'}R^{b'}$, $C_{3-10}$ cycloalkyl, $(C_{3-10}$ cycloalkyl)$C_{1-8}$ alkyl-, $C_{4-10}$ heterocycle, $(C_{4-10}$ heterocycle)$C_{1-8}$ alkyl-, $C_{6-10}$ aryl, $C_{6-10}$ aryloxy, $(C_{6-10}$ aryl)$C_{1-8}$ alkyl-, $C_{5-10}$ heteroaryl, and $(C_{5-10}$ heteroaryl)$C_{1-8}$ alkyl- and q is independently selected from: 0, 1, and 2.

In one embodiment, $R^{5'}$ is $C_{6-10}$ aryl (e.g., phenyl) optionally substituted with 0-5 $R^{5a}$ groups selected from $C_{1-10}$ alkoxy, $C_{3-8}$ cyclic alkoxy, halo-$C_{1-10}$ alkyl, nitro, cyano, $C_{1-8}$ alkyl, —$NO_2$, F, Cl, Br, I, —CN, $OR^{a'}$, $SR^{a'}$, $NR^{a'}R^{b'}$, $CF_3$, $OCF_3$, $COR^{a'}$, $CO_2R^{a'}$, $C(O)NR^{a'}R^{b'}$, $OC(O)R^{a'}$, $OCO_2R^{a'}$, $OC(O)NR^{a'}R^{b'}$, $NR^{b'}COR^{a'}$, $NR^{b'}CO_2R^{a'}$, $NR^{b'}C(O)NR^{a'}R^{b'}$, $S(O)_qNR^{a'}R^{b'}$, $C_{3-10}$ cycloalkyl, $(C_{3-10}$ cycloalkyl)$C_{1-8}$ alkyl-, $C_{4-10}$ heterocycle, $(C_{4-10}$ heterocycle)$C_{1-8}$ alkyl-, $C_{6-10}$ aryl, $C_{6-10}$ aryloxy, $(C_{6-10}$ aryl)$C_{1-8}$ alkyl-, $C_{5-10}$ heteroaryl, and $(C_{5-10}$ heteroaryl)$C_{1-8}$ alkyl- and q is independently selected from: 0, 1, and 2.

In yet another embodiment, each alkyl of $R^{5'}$ is interrupted by 0-2 groups selected from: $C(=O)$, O, S, $C(O)NR^{a'}$, $NR^{a'}C(O)$, and $NR^{a'}$.

In another embodiment, X' is a $C_{5-6}$ heteroaryl optionally substituted with 0-2 groups selected from $C_{1-8}$ alkyl, $C_{2-8}$ alkenyl, $C_{3-8}$ cycloalkyl, $(C_{3-8}$ cycloalkyl)$C_{1-8}$ alkyl-, $C_{3-8}$ cycloalkenyl, $(C_{3-8}$ cycloalkenyl)$C_{1-8}$ alkyl-, $C_{6-10}$ aryl, $(C_{6-10}$ aryl)$C_{1-8}$ alkyl-, $C_{5-10}$ heteroaryl, and $(C_{5-10}$ heteroaryl)$C_{1-8}$ alkyl-, wherein each alkyl or alkenyl group is interrupted by 0-2 groups selected from: O, S, and $N(R^{a'})$.

In another embodiment, provided herein is a compound of formula Ib or a stereoisomer or pharmaceutically acceptable salt thereof, wherein:

$R^{1'}$ and $R^{2'}$ independently are selected from: H, $C_{1-4}$ alkyl, $C_{3-6}$ cycloalkyl, and $(C_{3-6}$ cycloalkyl)$C_{1-2}$ alkyl-;

$R^{3'}$ is —$C_{1-4}$ alkyl- optionally substituted with 0-1 groups selected from F, Cl, OH, $OC_{1-2}$ alkyl, $CF_3$, and $OCF_3$; and, $R^{4'}$ and $R^{4''}$ are each independently selected from: H, —$C_{2-4}$ alkyl-$OR^{a'}$, —$C_{2-4}$ alkyl-$NR^{a'}R^{b'}$, $C_{1-6}$ alkyl, $C_{3-6}$ cycloalkyl, $(C_{3-6}$ cycloalkyl)$C_{1-4}$ alkyl-, phenyl, (phenyl)$C_{1-4}$ alkyl-, $C_{5-6}$ heteroaryl, and $(C_{5-6}$ heteroaryl)$C_{1-4}$ alkyl-, wherein each $R^{4'}$ or $R^{4''}$ group is optionally substituted with 0-2 $R^{4a'}$ when $R^{4'}$ and $R^{4''}$ are not hydrogen; and, $R^{4a'}$ is independently selected from F, Cl, —CN, OH, $OC_{1-4}$ alkyl, $CF_3$, $OCF_3$, $CO_2R^{a'}$, and $C(O)NR^{a'}R^{b'}$.

In another embodiment, provided herein is a compound of formula Ib or a stereoisomer or pharmaceutically acceptable salt thereof, wherein:

$R^{1'}$ and $R^{2'}$ are H;

$R^{3'}$ is —$CH_2$—; and, $R^{4'}$ and $R^{4''}$ are each independently selected from: H and $CH_3$.

In another embodiment, provided herein is a compound of formula Ib or a stereoisomer or pharmaceutically acceptable salt thereof, wherein:

X' is selected from: —$CH_2OR^{c'}$ and —$C(O)NR^{c'}R^{d'}$; or X' is a $C_{5-6}$ heteroaryl, optionally substituted with 0-1 groups selected $C_{1-4}$ alkyl, $C_{3-6}$ cycloalkyl, $(C_{3-6}$ cycloalkyl)$CH_2$—, phenyl, and benzyl;

$R^{c'}$ is selected from: H, methyl, ethyl, cyclopropyl and cyclobutyl; and, $R^{d'}$ is selected from: H and $C_{1-4}$ alkyl.

In another embodiment, provided herein is a compound of formula Ib or a stereoisomer or pharmaceutically acceptable salt thereof, wherein:

X' is selected from: —$CH_2OR^{c'}$ and —$C(O)NR^{c'}R^{d'}$;

$R^{c'}$ is selected from: methyl, ethyl, cyclopropyl and cyclobutyl; and, $R^{d'}$ is selected from: H and $CH_3$.

In another embodiment, provided herein is a compound of formula Ib or a stereoisomer or pharmaceutically acceptable salt thereof, wherein:

$R^{5'}$ is selected from: $C_{1-6}$ alkyl, $C_{3-6}$ cycloalkyl, $(C_{3-8}$ cycloalkyl)$C_{1-6}$ alkyl-, $C_{4-10}$ heterocycle, $(C_{4-10}$ heterocycle) $C_{1-6}$ alkyl-, $C_{6-10}$ aryl, $(C_{6-10}$ aryl)$C_{1-6}$ alkyl-, $C_{5-10}$ heteroaryl, and $(C_{5-10}$ heteroaryl)$C_{1-6}$ alkyl-, wherein each $R^{5'}$ group is optionally substituted with 0-2 $R^{5a'}$ and each alkyl of $R^{5'}$ is optionally interrupted by 0-2 groups selected from: $C(=O)$, O, S, $C(O)NR^{a'}$, $NR^{a'}C(O)$, and $NR^{a'}$;

$R^{5a'}$ is independently selected from $C_{1-4}$ alkyl, F, Cl, —CN, $OR^{a'}$, $SR^{a'}$, $NR^{a'}R^{b'}$, $CF_3$, $OCF_3$, $COR^{a'}$, $CO_2R^{a'}$, $C(O)NR^{a'}R^{b'}$, $OC(O)R^{a'}$, $NR^{b'}COR^{a'}$, $S(O)_qNR^{a'}R^{b'}$, $C_{3-6}$ cycloalkyl, $(C_{3-6}$ cycloalkyl)$C_{1-2}$ alkyl-, $C_{5-6}$ heterocycle, $(C_{5-6}$ heterocycle)$C_{1-2}$ alkyl-, $C_{6-10}$ aryl, $C_{6-10}$ aryloxy, $(C_{6-10}$ aryl)$C_{1-2}$ alkyl-, $C_{5-6}$ heteroaryl, and $(C_{5-6}$ heteroaryl)$C_{1-2}$ alkyl-;

$R^{a'}$ and $R^{b'}$ are each independently selected from H, $C_{1-4}$ alkyl, $(C_{1-8}$ alkoxy)$C_{1-8}$ alkyl-, $C_{3-6}$ cycloalkyl, $(C_{3-6}$ cycloalkyl)$C_{1-2}$ alkyl-, phenyl, (phenyl)$C_{1-2}$ alkyl-, $C_{5-6}$ heteroaryl, and $(C_{5-6}$ heteroaryl)$C_{1-2}$ alkyl-; or $R^{a'}$ and $R^{b'}$, together with the nitrogen to which they are attached, form a ring selected from pyrrolidino, piperidino, morpholino, and thiomorpholino ring.

In another embodiment, provided herein is a compound of formula Ib or a stereoisomer or pharmaceutically acceptable salt thereof, wherein:

$R^{5'}$ is selected from: $C_{1-6}$ alkyl, $C_{3-6}$ cycloalkyl, $(C_{3-8}$ cycloalkyl)$C_{1-6}$ alkyl-, $C_{5-6}$ heterocycle, $(C_{5-6}$ heterocycle) $C_{1-6}$ alkyl-, phenyl, (phenyl)$C_{1-6}$ alkyl-, $C_{5-6}$ heteroaryl, and $(C_{5-6}$ heteroaryl)$C_{1-6}$ alkyl-, wherein each $R^{5'}$ group is optionally substituted with 0-2 $R^{5a'}$ and each alkyl of $R^{5'}$ is optionally interrupted by 0-2 groups selected from: $C(=O)$, O, $C(O)NR^{a'}$, $NR^{a'}C(O)$, and $NR^{a'}$;

$R^{5a'}$ is independently selected from $C_{1-4}$ alkyl, F, Cl, $OR^{a'}$, $CF_3$, $OCF_3$, $COR^{a'}$, $C(O)NR^{a'}R^{b'}$, $C_{3-6}$ cycloalkyl, $(C_{3-6}$ cycloalkyl)$CH_2$—, phenyl, and benzyl;

$R^{a'}$ and $R^{b'}$ are each independently selected from H, $C_{1-4}$ alkyl, $(C_{1-4}$ alkoxy)$C_{1-4}$ alkyl-, $C_{3-6}$ cycloalkyl, $(C_{3-6}$ cycloalkyl)$CH_2$—, phenyl, and benzyl; or $R^{a'}$ and $R^{b'}$, together with the nitrogen to which they are attached, form a ring selected from pyrrolidino, piperidino, and morpholino.

In one embodiment, $R^1$ and $R^2$ are each hydrogen; X' is $C_{3-8}$ cycloalkyl (e.g., cyclopropyl); $R^{3'}$ is $C_1$ alkyl (e.g., methylene); $R^{4''}$ is hydrogen; $R^{4'}$ is $C_{1-10}$ alkyl, such as $C_1$ alkyl (e.g., methyl) or $C_2$ alkyl (e.g., ethyl); $R^{5'}$ is $C_{1-8}$ alkyl, for example, $C_1$ alkyl (e.g., methyl) or $C_2$ alkyl (e.g., ethyl, substituted with alkoxy, such as benzyloxy).

In one embodiment, $R^1$ and $R^2$ are each hydrogen; X' is $C_{3-8}$ cycloalkyl (e.g., cyclopropyl); $R^{3'}$ is $C_1$ alkyl (e.g., methylene); $R^{4''}$ is hydrogen; $R^{4'}$ is $C_{1-10}$ alkyl, such as $C_1$ alkyl (e.g., methyl) or $C_2$ alkyl (e.g., ethyl); $R^{5'}$ is $C_{6-10}$ aryl (e.g., phenyl).

In one embodiment, $R^1$ and $R^2$ are each hydrogen; X' is $C_{3-8}$ cycloalkyl (e.g., cyclopropyl); $R^{3'}$ is $C_1$ alkyl (e.g., methylene); $R^{4''}$ is hydrogen; $R^{4'}$ is $C_{1-10}$ alkyl, such as $C_1$ alkyl (e.g., methyl) or $C_2$ alkyl (e.g., ethyl); —$C_{2-6}$ alkyl-$OR^{a'}$ in which the alkyl is $C_2$ alkyl (e.g., ethyl) and $R^{a'}$ is $(C_{6-10}$ aryl)$C_{1-8}$ alkyl- in which the aryl is $C_6$ aryl (e.g., phenyl) and the alkyl is $C_1$ alkyl (e.g., methyl).

In one embodiment, $R^1$ and $R^2$ are each hydrogen; X' is $C_{3-8}$ cycloalkyl (e.g., cyclopropyl); $R^{3'}$ is $C_1$ alkyl (e.g., methylene); $R^{4''}$ is hydrogen; $R^{4'}$ is $(C_{3-8}$ cycloalkyl)$C_{1-8}$ alkyl- in which the alkyl is $C_1$ alkyl (e.g., methyl) and the cycloalkyl is $C_3$ cycloalkyl (e.g., cyclopropyl) and $R^{5'}$ is $C_{1-10}$ alkyl, for example, $C_1$ alkyl (e.g., methyl).

In one embodiment, $R^1$ and $R^2$ are each hydrogen; X' is $C_{3-8}$ cycloalkyl (e.g., cyclopropyl); $R^{3'}$ is $C_1$ alkyl (e.g., methylene); $R^{4''}$ is hydrogen; $R^{4'}$ is $C_{3-8}$ cycloalkyl, for example, $C_3$ cycloalkyl (e.g., cyclopropyl), $C_4$ cycloalkyl (e.g., cyclobutyl) or $C_5$ cycloalkyl (e.g., cyclopentyl); and $R^{5'}$ is $C_{1-10}$ alkyl, for example, $C_1$ alkyl (e.g., methyl).

In one embodiment, the adenosine $A_{2A}$ receptor agonist is a compound of Table 1 or a pharmaceutically acceptable salt thereof.

TABLE 1

| Compound Code | Chemical Structure |
| --- | --- |
| A | 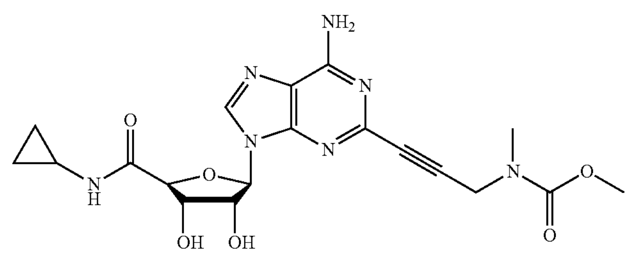 |
| B | 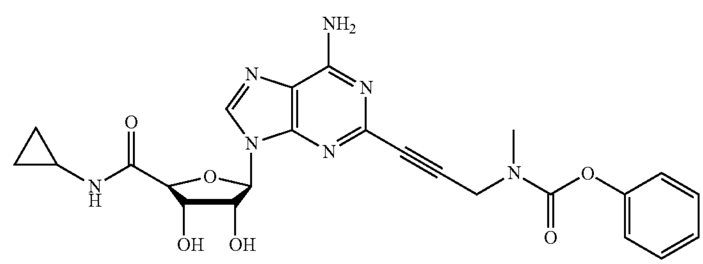 |

TABLE 1-continued

| Compound Code | Chemical Structure |
|---|---|
| C | 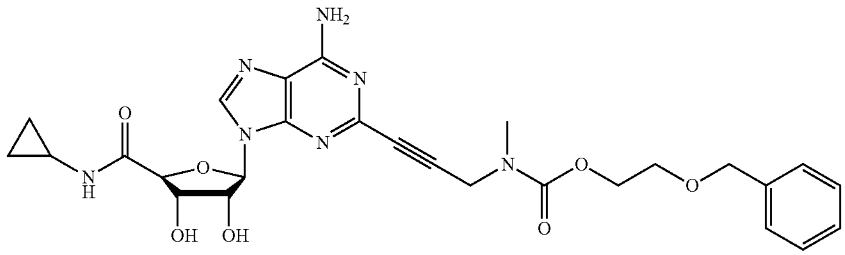 |
| D | 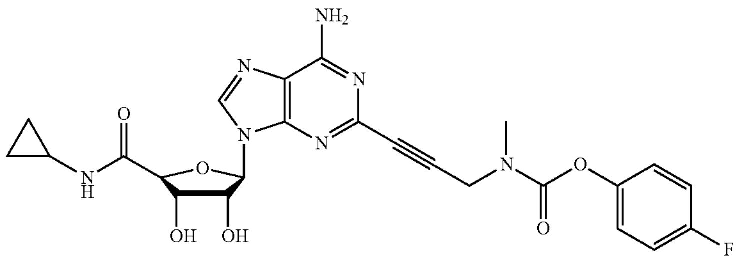 |
| E | 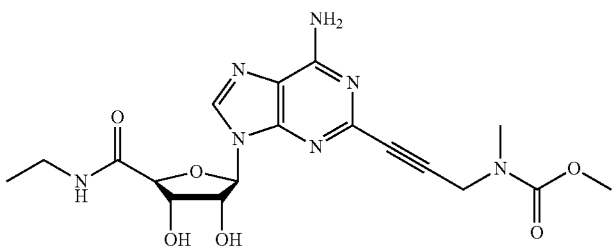 |
| F | 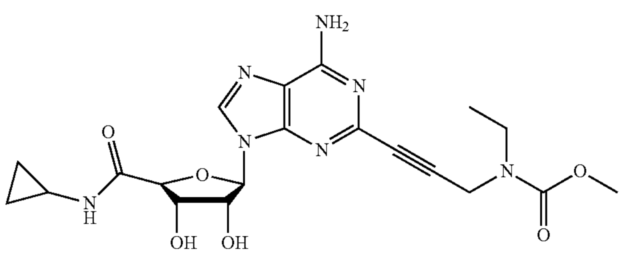 |
| G | 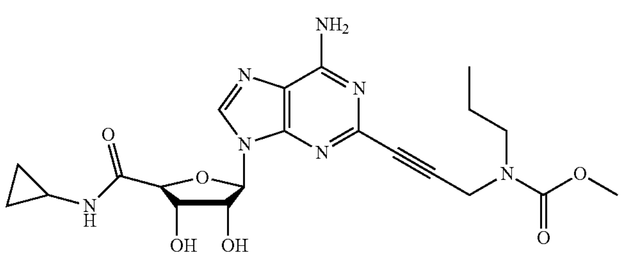 |
| H | 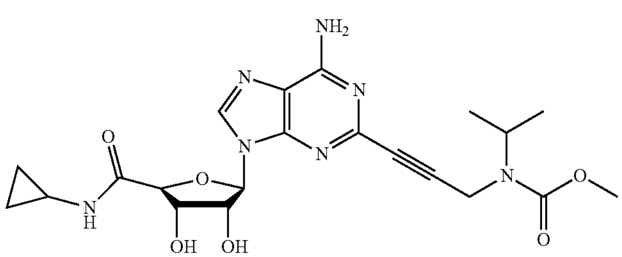 |

TABLE 1-continued

| Compound Code | Chemical Structure |
| --- | --- |
| I | 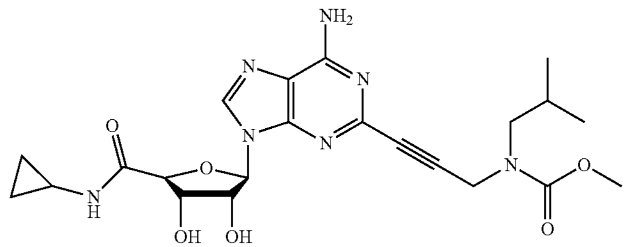 |
| J | 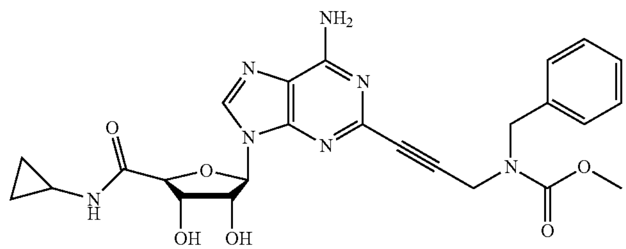 |
| K | 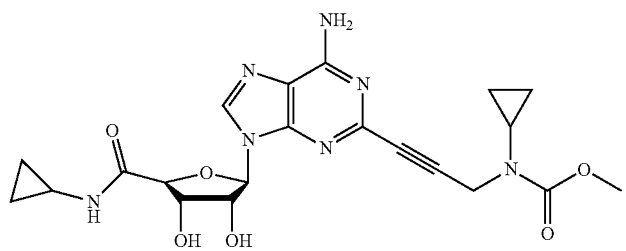 |
| L | 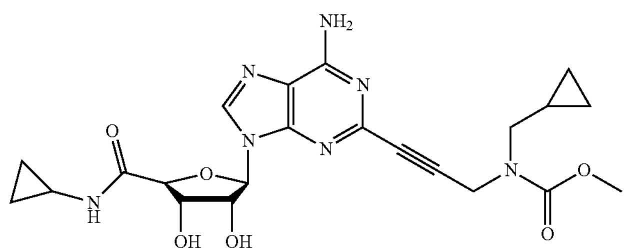 |
| M | 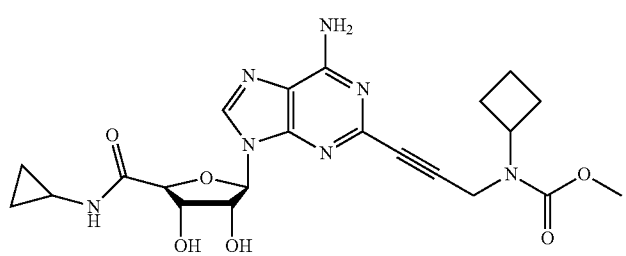 |
| N | 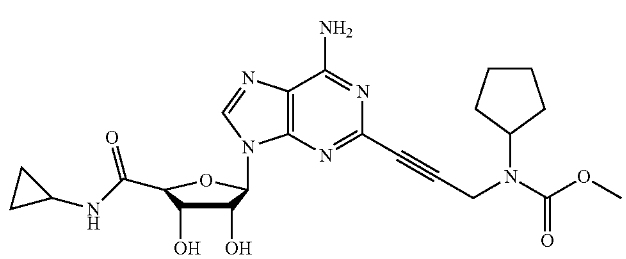 |

TABLE 1-continued
| Compound Code | Chemical Structure |
|---|---|
| O | 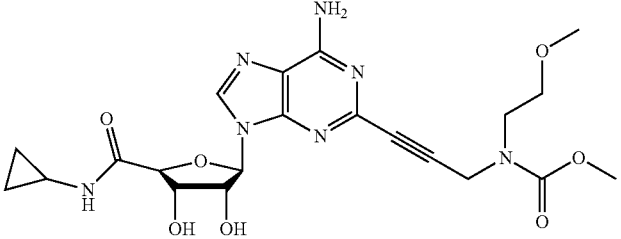 |
| P | 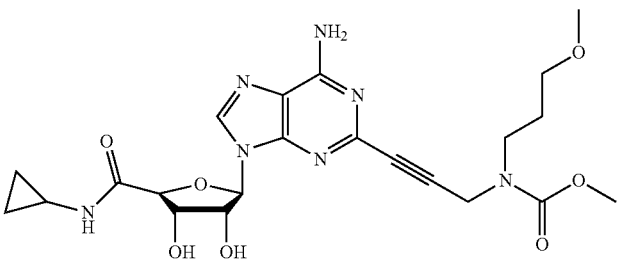 |
| Q | 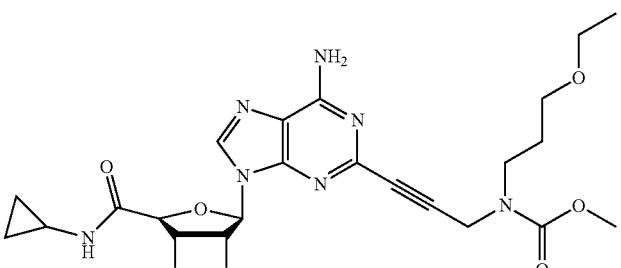 |
In one embodiment, the adenosine $A_{2A}$ receptor agonist is a compound of Table 2 or a pharmaceutically acceptable salt thereof.
TABLE 2
| Compound Code | Chemical Structure |
|---|---|
| R | 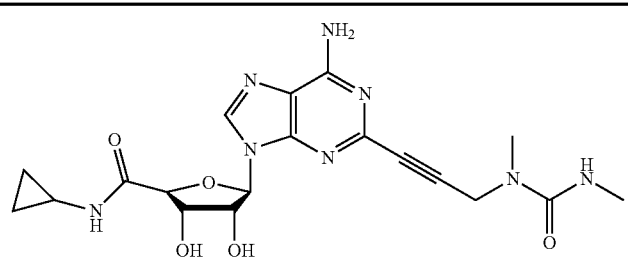 |
| S | 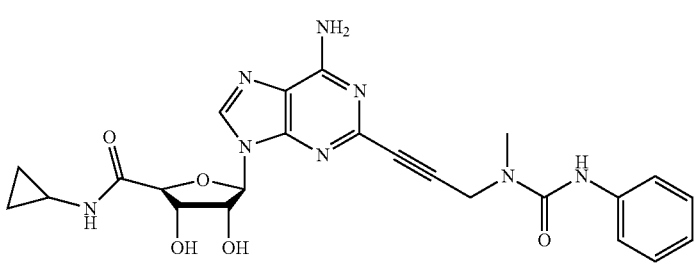 |

TABLE 2-continued
| Compound Code | Chemical Structure |
|---|---|
| T | 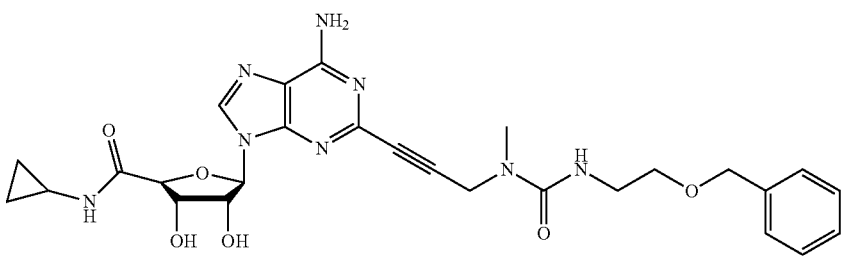 |
| U | 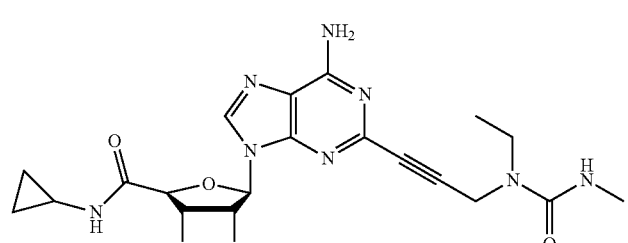 |
| V | 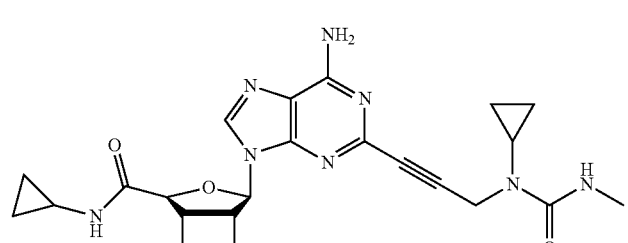 |
| W | 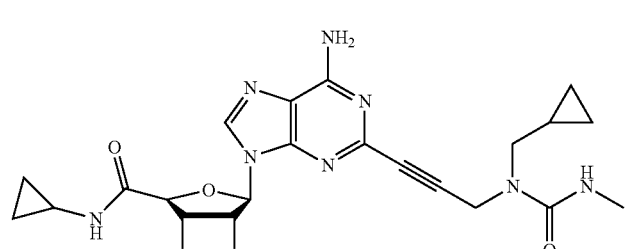 |
| X | 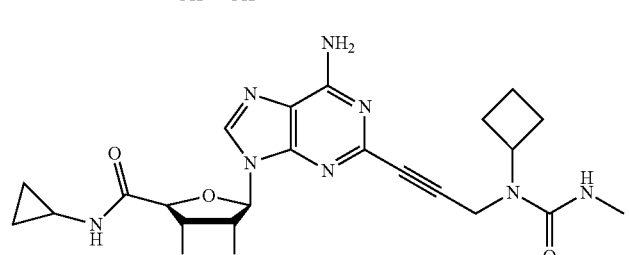 |
| Y | 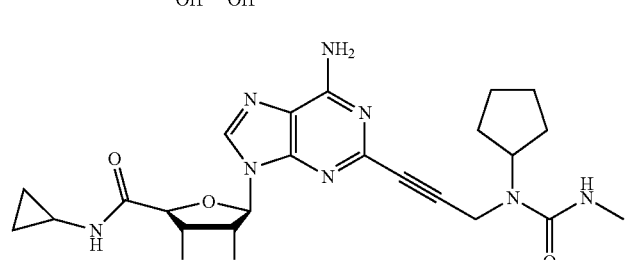 |

In one embodiment, the compounds disclosed herein are not a compound disclosed in U.S. Pat. No. 6,232,297; U.S. Pat. No. 7,214,665; U.S. Patent Application Publication No. 2006/004088; U.S. Patent Application Publication No. 2006/0217343; U.S. Patent Application Publication No. 2006/0040889; U.S. Patent Application Publication No. 2007/0270373; U.S. Pat. No. 6,914,053; U.S. Application Patent Publication No. 2006-0100169, International Application Publication No. WO 2006/015357; International Application Publication No. WO 2006/101920; International Application Publication No. WO 03/029264; Japanese Patent Application Publication No. 2002-536300; International Application Publication No. WO 06/074925; International Application publication No. WO 06/097260; U.S. Pat. No. 7,262,176; International Application Publication No. WO 05/117910; International Application Publication No. WO 06/045552; International Application Publication No. 03/051882; International Application Publication No. WO 03/061670; International Application No. WO 04/022573; U.S. Pat. No. 5,593,975; U.S. Patent Application Publication No. 2005245546; International Application Publication No. WO 01/62768; International Application Publication No. WO 04/069185 or International Application Publication No. WO 05/105803.

In another embodiment, the compound disclosed herein are not 4-{3-[6-amino-9-((2R,3R,4S,5S)-5-cyclopropylcarbamoyl-3,4-dihydroxytetrahydrofuran-2-yl)-9H-purin-2-yl]-2-propynyl}-piperidine-1-carboxylic acid methyl ester; 4-{3-[6-amino-9-((2R,3R,4S,5S)-5-ethylcarbamoyl-3,4-dihydroxytetrahydrofuran-2-yl)-9H-purin-2-yl]-2-propynyl}-piperidine-1-carboxylic acid methyl ester or 4-{3-[6-amino-9-((2R,3R,4S,5S)-5-ethylcarbamoyl-3,4-dihydroxytetrahydrofuran-2-yl)-9H-purin-2-yl]-2-propynyl}-piperidine-1-carboxylic acid isobutyl ester.

The compounds provided herein are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

Examples of the molecular weight of compounds provided herein can include (a) less than about 450, 500, 550, 600, 650, 700, 750, 800, 850, 900, 950, or 1000 grams per mole; (b) less than about 950 grams per mole; (c) less than about 800 grams per mole, and, (d) less than about 650 grams per mole.

The methods, compounds, and compositions/formulations provided herein are intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Such substituents can include, for example, alkyl, alkenyl, alkynyl, halogens, hydroxyl, aryl alkylcarbonyloxy, arylcarbonyloxy, alkoxycarbonyl oxy, aryloxycarbonyloxy, —COOH, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Stable means that the compound is suitable for pharmaceutical use.

The methods, compounds, and compositions/formulations provided herein covers stable compound and thus avoids, unless otherwise specified, the following bond types: heteroatom-halogen, N—S, O—S, O—O, and S—S.

The term "alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, n-hexyl, isopropyl, isobutyl, sec-butyl, tert-butyl, isopentyl, and s-pentyl. Moreover, the term alkyl includes both "unsubstituted alkyls" and "substituted alkyls," the latter of which refers to alkyl moieties having substituents replacing a hydrogen on one or more carbons of the hydrocarbon backbone.

The term "alkylene" includes organic radicals formed from an unsaturated aliphatic hydrocarbon. Examples of alkylenes include methylene, ethylene, propylene, butylenes and the like. The term alkylene includes both unsubstituted and substituted alkylenes, the latter of which refers to alkylenes having substitutents replacing a hydrogen on one or more carbons of the hydrocarbon backbone of the alkylene moiety.

The term "alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups. Moreover, the term "alkenyl" includes both "unsubstituted alkenyls" and "substituted alkenyls," the latter of which refers to alkenyl moieties having substituents replacing a hydrogen on one or more carbons of the hydrocarbon backbone.

The term "alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups. Moreover, the term "alkynyl" includes both "unsubstituted alkynyls" and "substituted alkynyls," the latter of which refers to alkynyl moieties having substituents replacing a hydrogen on one or more carbons of the hydrocarbon backbone.

The term "cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups. Specific examples thereof include cyclopropyl, cyclobutyl, cyclopentyl, cyclohexyl, cycloheptyl, cyclooctyl and the like. Cycloalkyl also include bicycloalkyl and tricycloalkyl, both of which include fused and bridged rings (e.g., norbornane and adamantane). Cycloalkyls can be further substituted, e.g., with the substituents described above.

The term "(cycloalkyl)alkyl" includes cycloalkyl and alkyl moieties as defined above where the cycloalkyl moiety and the alkyl moiety are linked via a carbon-carbon bond. Specific examples thereof include (cyclopropyl)methyl, (cyclopropyl)ethyl, (cyclobutyl)methyl, (cyclopentyl)methyl, (cyclohexyl)methyl, (cyclohexyl)ethyl, (cycloheptyl)methyl, (cyclooctyl)methyl and the like.

The term "(phenyl)alkyl" includes a phenyl moiety and an alkyl moiety, as defined above, linked via a carbon-carbon bond. Specific examples thereof include benzyl, phenethyl, (phenyl)propyl, (phenyl)isopropyl, (phenyl)butyl, (phenyl)pentyl, (phenyl) hexyl and the like.

The term "halo" or "halogen" includes fluoro, chloro, bromo, and iodo.

The term "aryl" includes any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, and tetrahydronaphthyl. The aromatic ring can be substituted at one or more ring positions with such substituents as described above.

The term "heteroaryl" includes stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any nitrogen or carbon atom that results in a stable structure. The heteroaryl rings described herein may be substituted on carbon or on a nitrogen atom if the resulting compound is stable.

Examples of heteroaryl moieties include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

The term "heterocycle" includes stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

Examples of heterocycles include, but are not limited to, decahydroquinolinyl, imidazolidinyl, imidazolinyl, indolinyl, isatinoyl, methylenedioxyphenyl, morpholinyl, octahydroisoquinolinyl, oxazolidinyl, oxindolyl, piperazinyl, piperidinyl, piperidonyl, 4-piperidonyl, piperonyl, pyranyl, pyrazolidinyl, pyrazolinyl, pyrrolidinyl, pyrrolinyl, tetrahydrofuranyl, tetrahydroisoquinolinyl, tetrahydroquinolinyl, 1-aza-bicyclo[2.2.2]octane, 2,5-diaza-bicyclo[2.2.2]octane, and 2,5-diaza-bicyclo[2.2.1]heptane. Also included are fused ring and spiro compounds containing, for example, the above heterocycles.

The term "alkoxy" includes both substituted and unsubstituted alkyl, alkenyl, and alkynyl groups covalently linked to an oxygen atom. Examples of alkoxy groups include methoxy, ethoxy, isopropyloxy, propoxy, t-butyloxy, isobutyloxy, butoxy, benzyloxy and pentoxy groups. The term alkoxy also includes substituted or unsubstituted cycloalkyl groups covalently linked to an oxygen atom.

In the case where there are geometrical isomers or optical isomers in the present compound, these isomers are also included in the scope of the methods, compounds, and compositions/formulations herein.

Further, the present compound may be in the form of a hydrate or a solvate. Further, in the case where there is tautomerism or polymorphism in the present compound, these compounds are also included in the scope of the methods, compounds, and compositions/formulations herein. In an embodiment, pharmaceutically active metabolites, salts, polymorphs, prodrugs, analogues, and/or derivatives of the adenosine A$_{2A}$ receptor agonist disclosed herein may be useful in the compositions and formulations.

The compounds provided herein may have a chiral center and may exist in and be isolated in optically active and racemic forms. Some compounds may exhibit polymorphism. The compounds provided herein encompasses any racemic, optically-active, polymorphic, or stereoisomeric form, or mixtures thereof, of a compound provided herein, which possess the useful properties described herein; it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine therapeutic activity using the standard tests described herein or using other similar tests which are well known in the art.

Specific and preferred values listed for radicals, substituents, and ranges, are for illustration only; they do not exclude other defined values or other values within defined ranges for the radicals and substituents.

3. Pharmaceutical Compositions, Formulations and Dosages

The adenosine A$_{2A}$ receptor agonists (e.g., a compound of formula Ia, formula Ib, formula 1 or one or more of Table 1 or one or more of Table 2) can be formulated as pharmaceutical compositions and administered to a subject, such as a human, in a variety of forms adapted to the chosen route of administration, e.g., orally or parenterally, by intravenous, intramuscular, topical, inhalation or subcutaneous routes. Exemplary pharmaceutical compositions are disclosed in "Remington: The Science and Practice of Pharmacy," A. Gennaro, ed., 20th edition, Lippincott, Williams & Wilkins, Philadelphia, Pa. Each of the adenosine $A_{2A}$ receptor agonists may be used alone or in combination as a part of a pharmaceutical composition of the invention.

In one embodiment, provided herein is a pharmaceutical composition comprising: a therapeutically effective amount of an adenosine $A_{2A}$ receptor agonist (e.g., a compound of formula Ia, formula Ib, formula 1 or one or more of Table 1 or one or more of Table 2) or a stereoisomer or pharmaceutically acceptable salt thereof and a pharmaceutically acceptable excipient.

The language "pharmaceutically acceptable salts" includes derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The "salt" of the present compound is not particularly limited as long as it is a pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumalic acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid or sulfosalicylic acid; quaternary ammonium salts such as methyl bromide, methyl iodide; salts with a halogen ion such as a bromine ion, a chlorine ion or an iodine ion; salts with an alkali metal such as lithium, sodium or potassium; salts with an alkaline earth metal such as calcium or magnesium; salts with a metal such as iron or zinc; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine or N,N-bis(phenylmethyl)-1,2-ethanediamine, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are used. Lists of suitable salts are found in *Remington's Pharmaceutical Sciences,* 18th ed., Mack Publishing Company, Easton, Pa., 1990, p 1445, the disclosure of which is hereby incorporated by reference.

In one embodiment, the pharmaceutical composition further comprises an anti-inflammatory compound. Examples of anti-inflammatory compounds include a Type IV phosphodiesterase inhibitor or another anti-inflammatory compound (e.g., other than a PDE inhibitor). The Type IV phosphodiesterase inhibitor may be, for example, rolipram, cilomilast, roflumilast, mesembrine, ibudilast, ONO6126, AWD12281, IC485, CP671305, HT0712, or GRC3886.

Also provided herein are pharmaceutical compositions that include an adenosine $A_{2A}$ receptor agonist in combination with one of more members selected from: (a) Leukotriene biosynthesis inhibitors, 5-lipoxygenase (5-LO) inhibitors, and 5-lipoxygenase activating protein (FLAP) antagonists selected from the group consisting of zileuton; ABT-761; fenleuton; tepoxalin; Abbott-79175; Abbott-85761; N-(5-substituted)-thiophene-2-alkylsulfonamides of Formula (5.2.8); 2,6-di-tert-butylphenol hydrazones of Formula (5.2.10); Zeneca ZD-2138 of Formula (5.2.11); SB-210661 of Formula (5.2.12); pyridinyl-substituted 2-cyanonaphthalene compound L-739,010; 2-cyanoquinoline compound L-746,530; indole and quinoline compounds MK-591, MK-886, and BAY×1005; (b) Receptor antagonists for leukotrienes LTB4, LTC4, LTD4, and LTE4 selected from the group consisting of phenothiazin-3-one compound L-651, 392; amidino compound CGS-25019c; benzoxazolamine compound ontazolast; benzenecarboximidamide compound BIIL 284/260; compounds zafirlukast, ablukast, montelukast, pranlukast, verlukast (MK-679), RG-12525, Ro-245913, iralukast (CGP 45715A), and BAY×7195; (d) 5-Lipoxygenase (5-LO) inhibitors; and 5-lipoxygenase activating protein (FLAP) antagonists; (e) Dual inhibitors of 5-lipoxygenase (5-LO) and antagonists of platelet activating factor (PAF); (f) Theophylline and aminophylline; (g) COX-1 inhibitors (NSAIDs); and nitric oxide NSAIDs; (h) COX-2 selective inhibitor rofecoxib; (i) Inhaled glucocorticoids with reduced systemic side effects selected from the group consisting of prednisone, predniso lone, flunisolide, triamcinolone acetonide, beclomethasone dipropionate, budesonide, fluticasone propionate, and mometasone furoate; (j) Platelet activating factor (PAF) antagonists; (k) Monoclonal antibodies active against endogenous inflammatory entities; (l) Anti-tumor necrosis factor (TNFα) agents selected from the group consisting of etanercept, infliximab, and D2E7; (m) Adhesion molecule inhibitors including VLA-4 antagonists; (n) Immunosuppressive agents selected from the group consisting of cyclosporine, azathioprine, and methotrexate; or (O) anti-gout agents selected from the group consisting of colchicines.

In some embodiments, the adenosine $A_{2A}$ receptor agonist (e.g., a compound of formula Ia, formula Ib, formula 1 or one or more of Table 1 or one or more of Table 2) is administered in combination with a therapeutic agent or procedure that treats glaucoma or ocular hypertension. Examples of such agents include alpha agonists (e.g., apraclonidine HCl, brimonidine tartrate), carbonic anhydrase inhibitors (e.g., brinzolamide, dorzolamide HCl, acetazolamide), prostaglandin analogs (e.g., travaprost, bimatoprost, latanoprost), beta blockers (e.g., timolol, betaxolol, levobunolol, metipranolol) and cholinergics (e.g., polocarpine HCl or carbachol). Examples of procedures that treat glaucoma or ocular hypertension include laser surgery, filtering microsurgery, glaucoma implants (e.g., shunts) or laser iridotomy.

When an adenosine $A_{2A}$ receptor agonist (e.g., a compound of formula Ia, formula Ib, formula 1 or one or more of Table 1 or one or more of Table 2) is administered in combination with another agent or agents (e.g., co-administered), then the adenosine $A_{2A}$ receptor agonist (e.g., a compound of formula Ia, formula Ib, formula 1 or one or more of Table 1 or one or more of Table 2) and other agent can be administered simultaneously or in any order. They can be administered as a single pharmaceutical composition or as separate compositions. The administration of the adenosine $A_{2A}$ receptor agonist ((e.g., a compound of formula Ia, formula Ib, formula 1 or one or more of Table 1 or one or more of Table 2) can be prior to the other agent(s), within minutes thereof, or up to about hours (e.g., 24 or 48) after the administration of the other agent(s). For example, the administration of the adenosine $A_{2A}$ receptor agonist (e.g., a compound of formula Ia, formula Ib, formula 1 or one or more of Table 1 or one or more of Table 2) can be within about 24 hours or within about 12 hours.

The term "pharmaceutically acceptable excipient" includes any excipient that is suitable for administration to a subject.

The adenosine $A_{2A}$ receptor agonists (e.g., a compound of formula Ia, formula Ib, formula 1 or one or more of Table 1 or one or more of Table 2) can be formulated as pharmaceutical compositions and administered to a mammalian host, such as a human subject in a variety of forms adapted to the chosen route of administration, e.g., orally or parenterally, by intravenous, intrathecally, intramuscular, topical, inhalation or subcutaneous routes. Exemplary pharmaceutical compositions are disclosed in "Remington: The Science and Practice of Pharmacy," A. Gennaro, ed., 20th edition, Lippincott, Williams & Wilkins, Philadelphia, Pa.

Thus, the present compounds may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The preventive or therapeutic adenosine $A_{2A}$ receptor agonists (e.g., a compound of formula Ia, formula Ib, formula 1 or one or more of Table 1 or one or more of Table 2) for treating glaucoma or ocular hypertension can be administered, e.g., either orally or parenterally. Examples of the dosage form include eye drops, ophthalmic ointments, injections, tablets, capsules, granules, powders and the like. In one embodiment, the dosage is in the form of eye drops. These can be prepared using any of generally used techniques. For example, in the case of eye drops, a desired eye drop can be prepared by adding the present compound to purified water or a buffer or the like, stiffing the mixture, and then adjusting the pH of the solution with a pH adjusting agent. Further, an additive which is generally used in eye drops can be used as needed. For example, preparation thereof can be carried out using a tonicity agent such as sodium chloride or concentrated glycerin, a buffer such as sodium phosphate, sodium acetate, boric acid, borax or citric acid, a surfactant such as polyoxyethylene sorbitan monooleate, polyoxyl stearate or polyoxyethylene hydrogenated castor oil, a stabilizer such as sodium citrate or sodium edetate, a preservative such as benzalkonium chloride or paraben, and the like. The pH of the eye drops is permitted as long as it falls within the range that is acceptable as an ophthalmic preparation. In one embodiment, the pH range is from 3 to 8. The ophthalmic ointments can be prepared with a generally used base such as white petrolatum or liquid paraffin. Also, oral preparations such as tablets, capsules, granules and powders can be prepared by adding an extender such as lactose, crystalline cellulose, starch or vegetable oil, a lubricant such as magnesium stearate or talc, a binder such as hydroxypropyl cellulose or polyvinyl pyrrolidone, a disintegrant such as carboxymethyl cellulose calcium or low-substituted hydroxypropylmethyl cellulose, a coating agent such as hydroxypropylmethyl cellulose, macrogol or a silicone resin, a film forming agent such as gelatin film, and the like, as needed.

The compositions and preparations of the adenosine $A_{2A}$ receptor agonists (e.g., a compound of formula Ia, formula Ib, formula 1 or one or more of Table 1 or one or more of Table 2) may contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. In the case of an eye drop, an eye drop containing an active ingredient at a concentration of generally from 0.000001 to 10% (w/v), 0.00001 to 3% (w/v), 0.0001 to 1% (w/v), or 0.001 to 0.1% (w/v) may be instilled to an adult once to several times a day. In the case of oral administration, the present compound may be administered to an adult once or divided into several times at a dose of generally from 0.01 to 5000 mg per day, 0.1 to 2500 mg per day, or 1 to 1000 mg per day.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The adenosine $A_{2A}$ receptor agonists (e.g., a compound of formula Ia, formula Ib, formula 1 or one or more of Table 1 or one or more of Table 2) may also be administered intravenously or intraperitoneally by infusion or injection. Solutions of the adenosine $A_{2A}$ receptor agonists (e.g., a compound of formula Ia, formula Ib, formula 1 or one or more of Table 1 or one or more of Table 2) or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, isotonic agents, for example, sugars, buffers or sodium chloride, are included. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation include vacuum drying and the freeze drying techniques, which yield a powder of the active ingredient plus any additional desired ingredient present in the previously sterile-filtered solutions.

For topical administration, the adenosine $A_{2A}$ receptor agonists (e.g., a compound of formula Ia, formula Ib, formula 1 or one or more of Table 1 or one or more of Table 2) may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the adenosine $A_{2A}$ receptor agonists (e.g., a compound of formula Ia, formula Ib, formula 1 or one or more of Table 1 or one or more of Table 2) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the adenosine $A_{2A}$ receptor agonists ((e.g., a compound of formula Ia, formula Ib, formula 1 or one or more of Table 1 or one or more of Table 2) in a liquid composition, such as a lotion, will be from (a) about 0.1-25 wt % and (b) about 0.5-10 wt %. The concentration in a semi-solid or solid composition such as a gel or a powder will be (a) about 0.1-5 wt % and (b) about 0.5-2.5 wt %.

The amount of the adenosine $A_{2A}$ receptor agonist (e.g., a compound of formula Ia, formula Ib, formula 1 or one or more of Table 1 or one or more of Table 2) or an active salt or derivative thereof, required for use in treatment will vary not only with the particular compound or salt selected but also with the route of administration, the nature of the condition being treated, and the age and condition of the patient and will be ultimately at the discretion of the attendant physician or clinician. In general, however, a suitable dose will be in the range of from (a) about 1.0-100 mg/kg of body weight per day, (b) about 10-75 mg/kg of body weight per day, or (c) about 5-20 mg/kg body weight per day.

The adenosine $A_{2A}$ receptor agonists (e.g., a compound of formula Ia, formula Ib, formula 1 or one or more of Table 1 or one or more of Table 2) can be conveniently administered in unit dosage form; e.g., tablets, caplets, etc., containing (a) about 4-400 mg, (b) about 10-200 mg, or (c) about 20-100 mg of active ingredient per unit dosage form.

In one embodiment, the adenosine $A_{2A}$ receptor agonists (e.g., a compound of formula Ia, formula Ib, formula 1 or one or more of Table 1 or one or more of Table 2) is administered to achieve peak plasma concentrations of the active compound of from (a) about 0.02-20 µM, (b) about 0.1-10 µM, or (c) about 0.5-5 µM. These concentrations may be achieved, for example, by the intravenous injection of a 0.005-0.5% solution of the active ingredient, or orally administered as a bolus containing about 4-400 mg of the active ingredient.

The adenosine $A_{2A}$ receptor agonists (e.g., a compound of formula Ia, formula Ib, formula 1 or one or more of Table 1 or one or more of Table 2) can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) Mack Publishing Co.

The desired dose of the adenosine $A_{2A}$ receptor agonists (e.g., a compound of formula Ia, formula Ib, formula 1 or one or more of Table 1 or one or more of Table 2) may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The examples provided in this application are non-inclusive unless otherwise stated. They include but are not limited to the recited groups.

All patents, patent applications, books and literature cited in the specification are hereby incorporated by reference in their entirety. In the case of any inconsistencies, the present disclosure, including any definitions therein will prevail.

The invention will be further described by reference to the following detailed examples, which are given for illustration of the invention, and are not intended to be limiting thereof.

EXAMPLES

I. Synthesis and Characterization

The following abbreviations have been used herein:
$^{125}$I-ABA N$^6$-(4-amino-3-$^{125}$iodo-benzyl)adenosine
DCM dichloromethane
DMF dimethylformamide
DMSO dimethylsulfoxide
DMSO-d$_6$ deuterated dimethylsulfoxide
eq equivalent
$^{125}$I-APE, 2-[2-(4-amino-3-[$^{125}$I]iodophenyl)ethylamino] adenosine;
HPLC high-performance liquid chromatography
$^{125}$I-ZM241385, $^{125}$I-4-(2-[7-amino-2-[2-furyl][1,2,4] triazolo[2,3-a][1,3,5]triazin-5-yl-amino]ethyl)phenol;
LC/MS liquid chromatography/mass spectrometry
LRMS low resolution mass spectrometry
m.p. melting point
MHz megahertz
NECA N-ethylcarboxamidoadenosine
NMR nuclear magnetic resonance
TFA trifluoroacetic acid.

Nuclear magnetic resonance spectra for proton ($^1$H NMR) were recorded on a 300 MHz Varian Gemini 2000 (or similar instrument) spectrophotometer. The chemical shift values are expressed in ppm (parts per million) relative to tetramethylsilane. For data reporting, s=singlet, d=doublet, t=triplet, q=quartet, and m=multiplet. Mass spectra were measured on a Finnigan LCQ Advantage. Analytical HPLC was done on a Shimazdu LC10 or LC20 Systemtimes. 150 mm) as as described below. Preparative HPLC was performed on a Shimadzu Discovery HPLC with a Shim-pack VP-ODS C18 (20×100 mm) column operated at room temperature. Compounds were eluted at 30 mL/min with a gradient 20-80% of water (containing 0.1% TFA) to methanol over 15 minutes with UV detection at 254 nm using a SPD10A VP Tunable detector. All final compounds presented here were determined to be greater than 98% pure by HPLC. Flash chromatography was performed on Silicyle 60A gel (230-400 mesh) or using reusable chromatography columns and system from RT Scientific, Manchester N.H. All reactions were done under a nitrogen atmosphere in flame-dried glassware unless otherwise stated.

Synthesis of Alkyne Substituents
Compounds of Formula Ia—Representative Procedure for Alkyne Preparation Containing an N-Methyl: A solution of N-methyl-propargylamine (2.81 mmol) in anhydrous DCM (25 mL) was cooled over ice. The corresponding chloroformate (9.95 mmol) and triethylamine (4.27 mmol) were added, the ice was removed, and the mixture stirred at 24° C. for 20 h. The DCM was removed, and the mixture taken up in ethyl acetate (100 mL), washed with water (100 mL), dried (MgSO$_4$), and filtered. The crude mixture was adhered to silica and purified by column chromatography, eluting with a gradient of hexanes.

Compounds of Formula Ia—Representative Procedure for Alkyne Preparation Containing Various N-Propargyl-N-Substituents:

Scheme 1 illustrates a representative procedure for alkyne preparation:

A suspension of the substituted primary amine (11.27 mmol), substituted chloroformate (24.53 mmol) and potassium carbonate (17.84 mmol) in diethyl ether (25 ml)/water (15 ml) was stirred at 24° C. for 23 h. Ether (200 mL) is added and the mixture extracted with water (2×200 mL). The aqueous layer was back extracted with DCM (2×150 mL), the organic extracts dried over MgSO$_4$, filtered, and evaporated to dryness to afford the crude product. The crude was adhered to silica and purified via a silica plug, eluting with DCM (150 mL) and DCM/MeOH (2%, 250 mL). The later fraction was evaporated to dryness to afford the desired intermediate carbamate with yields up to 70%. One of skill in the art would be able to determine the appropriate primary amine and chloroformate to use in order to obtain the desired intermediate carbamate.

The intermediate carbamate (7.51 mmol), potassium hydroxide (24.24 mmol), 80% propargyl bromide in toluene (23.34 mmol), and tetrabutylammonium bromide (1.538 g, 4.77 mmol were stirred in toluene (35 mL) at 24° C. for 72 h. The mixture was filtered, toluene (25 mL) was added and the solution washed with water (3×75 mL). The organic layers were dried over MgSO$_4$, filtered, adhered to silica and purified by silica column chromatography, eluting with hexanes/ethyl acetate gradient (0-30% EtOAc). Like fractions were collected to afford the pure desired carbamate with yields up to 71%.

Scheme 1

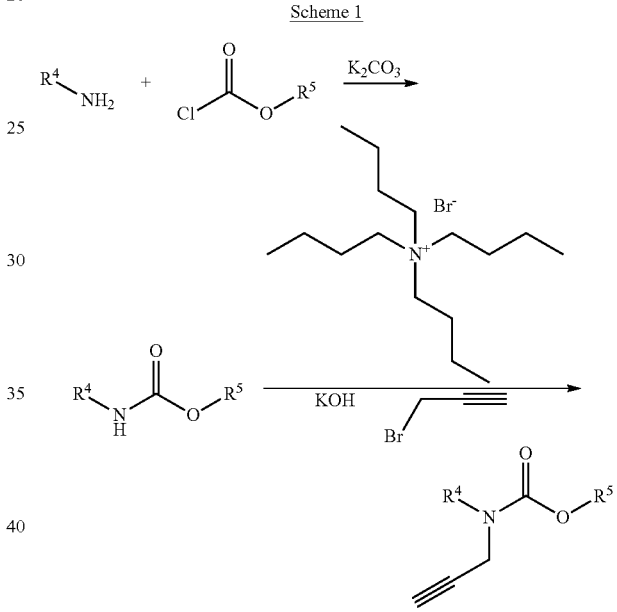

Methyl methyl(prop-2-ynyl)carbamate

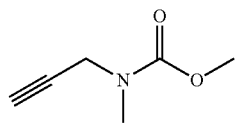

Using the representative procedure for alkyne preparation containing an N-methyl described above, N-methyl-propargylamine (410 mg) gave the product as a light yellow oil: yield 536 mg, 75%. LRMS ESI (M+H$^+$) 128.2. HPLC rt=6.1 min.

Phenyl methyl(prop-2-ynyl)carbamate

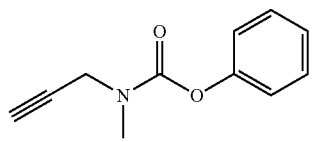

Using the representative procedure for alkyne preparation containing an N-methyl described above, N-methyl-propargylamine (205 mg) gave the product as a light yellow oil: yield 530 mg, 100%. LRMS ESI (M+H$^+$) 190.2. HPLC rt=6.7 min 2-(Benzyloxy)ethyl methyl(prop-2-ynyl)carbamate

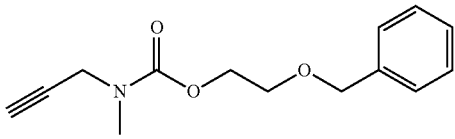

Using the representative procedure for alkyne preparation containing an N-methyl described above, N-methyl-propargylamine (205 mg) gave the product as a light yellow oil: yield 696 mg, 100%. LRMS ESI (M+H$^+$) 248.3. HPLC rt=7.7 min 4-Fluorophenyl methyl(prop-2-ynyl)carbamate

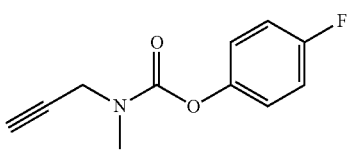

Using the representative procedure for alkyne preparation containing an N-methyl described above, N-methyl-propargylamine (205 mg) gave the product as a clear oil: yield 583 mg, 100%. LRMS ESI (M+H$^+$) 208.2. HPLC rt=8.7 min.

Methyl 2-methoxyethyl(prop-2-ynyl)carbamate

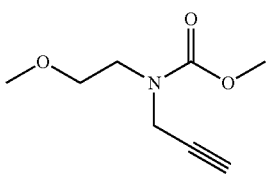

Using the representative procedure for alkynes containing various N-substituent described above, 2-methoxyethanamine (1.00 ml, 11.27 mmol), gave the product as a light yellow oil: yield 914 mg, 50% overall yield. LRMS ESI (M+H$^+$) 171.9. HPLC rt=5.9 min.

Synthesis of Select Compounds

Representative Procedure for C2 Coupling: To a solution of N-cyclopropyl 2-iodocarboxamidoadenosine (0.208 mmol) in freshly degassed DMF (20 mL) was added degassed triethylamine (3.56 mmol), Pd(PPh$_3$)$_4$ (0.030 mmol), CuI (catalytic), and the corresponding alkyne (2.11 mmol). The mixture was stirred at room temperature under and inert atmosphere for 20 h. Silica bound Pd(II) scavenger Si-thiol (241 mg) and Pd(0) scavenger Si-TAAcOH (642 mg) were added and stirring continued a further 48 h. The suspension was filtered through celite and the resulting solution evaporated to dryness. The crude was purified by column chromatography, eluting with a gradient of DCM/MeOH to afford the pure product.

The intermediate products of the present compound, for instance, the iodecarboxamidoadenosine derivative can be produced according to a common procedure in the field of organic synthetic chemistry, and also can be produced based on the method described in International Application Publication No. WO 2003/029264, Japanese Patent Application No. 2005-508933, International Application Publication Nos. WO 2006/015357 and WO 2007/136817 or Japanese Patent Application No. 2002-536300.

Representative Procedure for the Synthesis of the Compounds of Formula Ib

Scheme 2

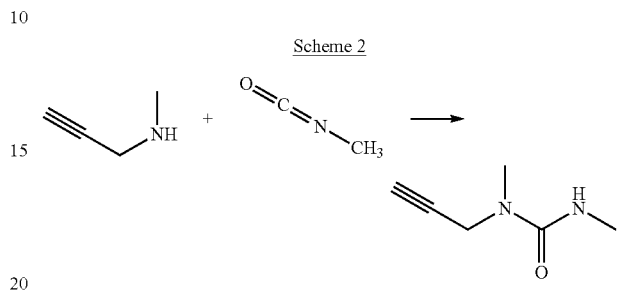

The urea-alkynes of Formula Ib can be made, as shown in Scheme 2, by the reaction of the appropriate amino alkynyl (e.g. N-methyl-propargylamine) with the corresponding isocyanates. The resulting alkynes can be reacted with the iodecarboxamidoadenosine intermediate similar to the carbamates compounds of Formula Ia.

Example 1

N-Cyclopropyl 2-{3-[methoxycarbonyl(methyl)amino]propyn-1-yl}adenosine-5'-uronamide

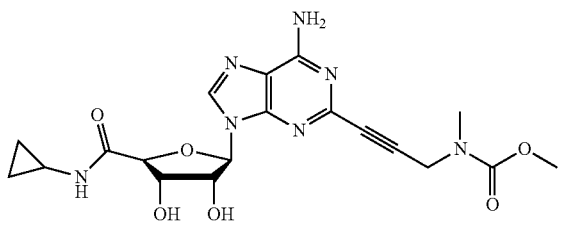

Using the representative procedure for C2-coupling above, N-cyclopropyl 2-iodocarboxamidoadenosine (95 mg) gave the title compound as a white solid: yield 49 mg, 51%. LRMS ESI (M+H$^+$) 446.2. HPLC rt=4.7 min $^1$H NMR (300 MHz, CD$_3$OD) δ[8.42, s, 1H][6.01, d, J=6.9, 1H][4.82, m, 1H][4.38, m, 2H][4.37, s, 2H][3.71, s, 3H][3.03, s, 3H][2.68, m, 1H][0.75, d, J=6.3, 2H][0.5, m, 2H].

Example 2

N-Cyclopropyl 2-{3-[phenoxycarbonyl(methyl)amino]propyn-1-yl}adenosine-5'-uronamide

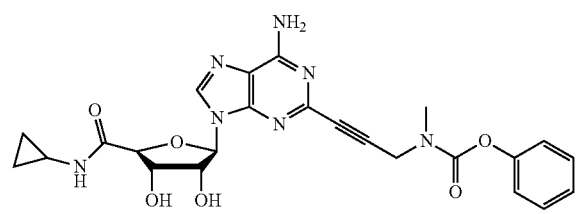

Using the representative procedure for C2-coupling above, N-cyclopropyl 2-iodocarboxamidoadenosine (93 mg) gave the title compound as a white solid: yield 31 mg, 29%. LRMS ESI (M+H$^+$) 508.3. HPLC rt=6.6 min.

Example 3

N-Cyclopropyl 2-{3-[2-((benzyloxy)ethoxycarbonyl)(methyl)amino]propyn-1-yl}adenosine-5'-uronamide

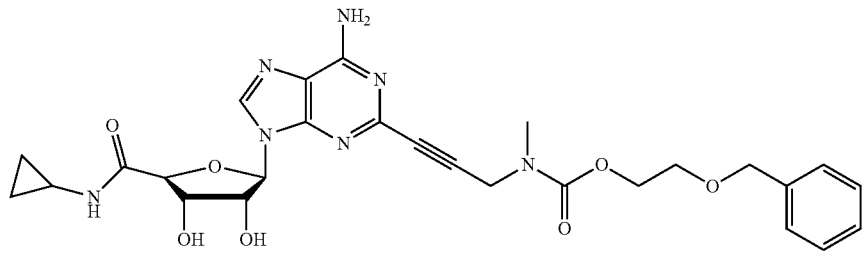

Using the representative procedure for C2-coupling above, N-cyclopropyl 2-iodocarboxamidoadenosine (135 mg) gave the title compound as a white solid: yield 100 mg, 58%. LRMS ESI (M+H$^+$) 566.3. HPLC rt=7.1 min.

Example 4

N-Cyclopropyl 2-{3-[4-fluorophenoxycarbonyl(methyl)amino]propyn-1-yl}adenosine-5'-uronamide

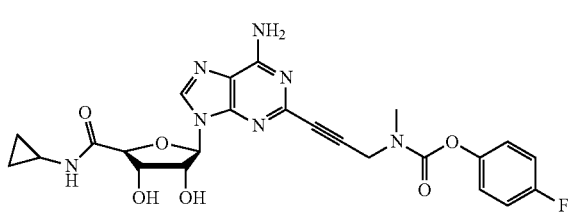

Using the representative procedure for C2-coupling above, N-cyclopropyl 2-iodocarboxamidoadenosine (83 mg) gave the title compound as a white solid: yield 26 mg, 26%. LRMS ESI (M+H$^+$) 526.2. HPLC rt=6.7 min.

Example 5

N-Ethyl 2-{3-[methoxycarbonyl(methyl)amino]propyn-1-yl}adenosine-5'-uronamide

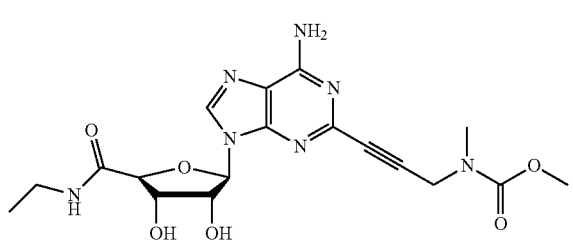

Using the representative procedure for C2-coupling above, N-cyclopropyl 2-iodocarboxamidoadenosine (105 mg) gave the title compound as a white solid: yield 35 mg, 33%. LRMS ESI (M+H$^+$) 434.2. HPLC rt=8.5 min.

Example 6

N-Cyclopropyl 2-{3-[4-(ethyl(methoxycarbonyl)amino)]propyn-1-yl}adenosine-5'-uronamide

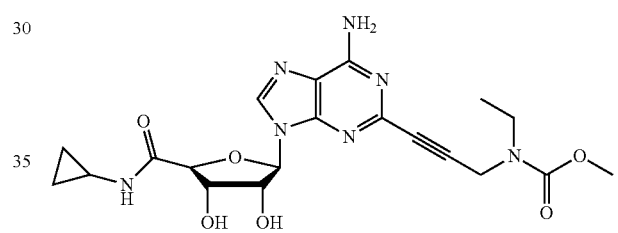

Using the representative procedure for C2-coupling above, N-cyclopropyl 2-iodocarboxamidoadenosine (99 mg) gave the title compound as an off white solid: yield 58 mg, 57%. LRMS ESI (M+H$^+$) 460.1. HPLC rt=9.1 min.

Example 7

N-Cyclopropyl 2-{3-[4-(methoxycarbonyl(propyl)amino)]propyn-1-yl}adenosine-5'-uronamide

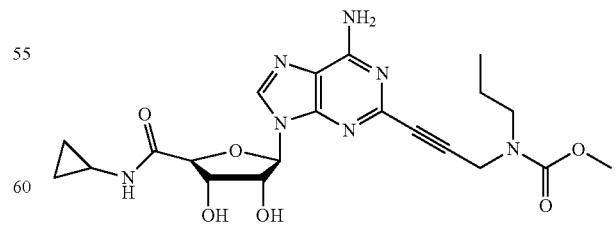

Using the representative procedure for C2-coupling above, N-cyclopropyl 2-iodocarboxamidoadenosine (96 mg) gave the title compound as an off white solid: yield 44 mg, 43%. LRMS ESI (M+H$^+$) 474.2. HPLC rt=9.9 min.

Example 8

N-Cyclopropyl 2-{3-[4-(isopropyl(methoxycarbonyl)amino)]propyn-1-yl}adenosine-5'-uronamide

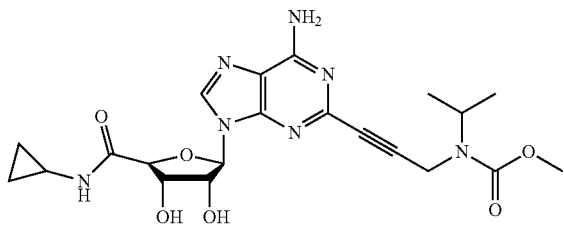

Using the representative procedure for C2-coupling above, N-cyclopropyl 2-iodocarboxamidoadenosine (94 mg) gave the title compound as an off white solid: yield 45 mg, 45%. LRMS ESI (M+H$^+$) 474.2. HPLC rt=9.6 min.

Example 9

N-Cyclopropyl 2-{3-[4-(isobutyl(methoxycarbonyl)amino)]propyn-1-yl}adenosine-5'-uronamide

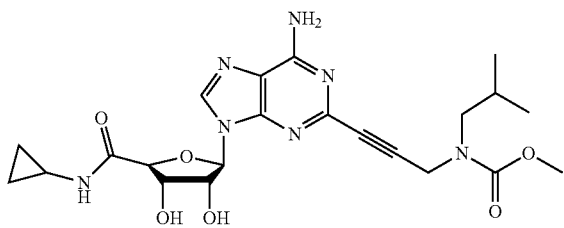

Using the representative procedure for C2-coupling above, N-cyclopropyl 2-iodocarboxamidoadenosine (101 mg) gave the title compound as an off white solid: yield 86 mg, 78%. LRMS ESI (M+H$^+$) 488.1. HPLC rt=10.8 min.

Example 10

N-Cyclopropyl 2-{3-[4-(benzyl(methoxycarbonyl)amino)]propyn-1-yl}adenosine-5'-uronamide

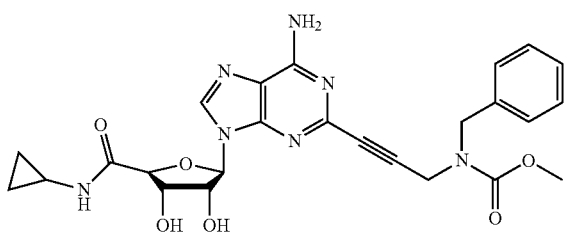

Using the representative procedure for C2-coupling above, N-cyclopropyl 2-iodocarboxamidoadenosine (95 mg) gave the title compound as an off white solid: yield 69 mg, 62%. LRMS ESI (M+H$^+$) 522.1. HPLC rt=11.2 min.

Example 11

N-Cyclopropyl 2-{3-[4-(cyclopropyl(methoxycarbonyl)amino)]propyn-1-yl}adenosine-5'-uronamide

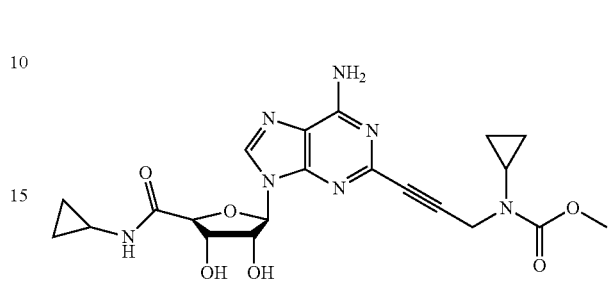

Using the representative procedure for C2-coupling above, N-cyclopropyl 2-iodocarboxamidoadenosine (74 mg) gave the title compound as an off white solid: yield 47 mg, 60%. LRMS ESI (M+H$^+$) 472.1. HPLC rt=9.3 min.

Example 12

N-Cyclopropyl 2-{3-[4-(cyclopropylmethyl(methoxycarbonyl)amino)]propyn-1-yl}adenosine-5'-uronamide

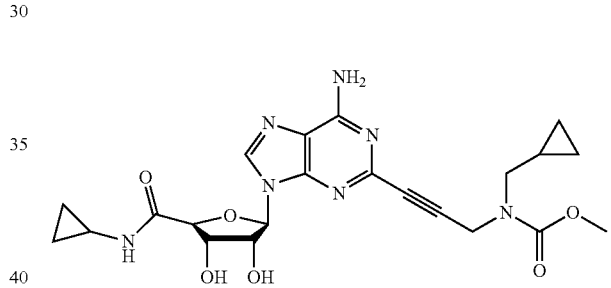

Using the representative procedure for C2-coupling above, N-cyclopropyl 2-iodocarboxamidoadenosine (99 mg) gave the title compound as an off white solid: yield 60 mg, 56%. LRMS ESI (M+H$^+$) 486.2. HPLC rt=10.2 min.

Example 13

N-Cyclopropyl 2-{3-[4-(cyclobutyl(methoxycarbonyl)amino)]propyn-1-yl}adenosine-5'-uronamide

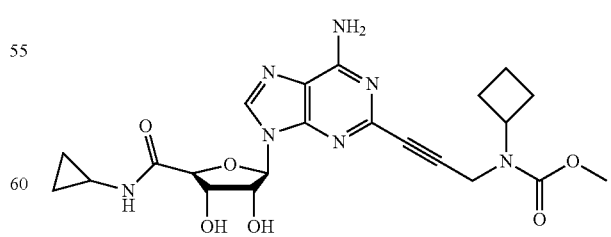

Using the representative procedure for C2-coupling above, N-cyclopropyl 2-iodocarboxamidoadenosine (104 mg) gave the title compound as an off white solid: yield 67 mg, 59%. LRMS ESI (M+H$^+$) 486.2. HPLC rt=10.3 min.

Example 14

N-Cyclopropyl 2-{3-[4-(cyclopentyl(methoxycarbonyl)amino)]propyn-1-yl}adenosine-5'-uronamide

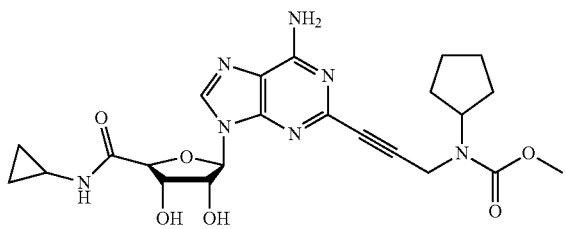

Using the representative procedure for C2-coupling above, N-cyclopropyl 2-iodocarboxamidoadenosine (76 mg) gave the title compound as an off white solid: yield 60 mg, 70%. LRMS ESI (M+H$^+$) 500.2. HPLC rt=10.9 min.

Example 15

N-Cyclopropyl 2-{3-[4-(methoxycarbonyl(2-methoxyethyl)amino)]propyn-1-yl}adenosine-5'-uronamide

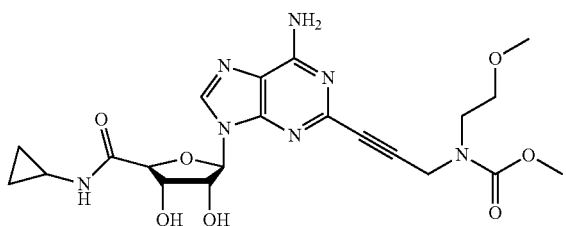

Using the representative procedure for C2-coupling above, N-cyclopropyl 2-iodocarboxamidoadenosine (99 mg) gave the title compound as an off white solid: yield 32 mg, 30%. LRMS ESI (M+H$^+$) 490.2. HPLC rt=8.6 min

Example 16

N-Cyclopropyl 2-{3-[4-(methoxycarbonyl(3-methoxypropyl)amino)]propyn-1-yl}adenosine-5'-uronamide

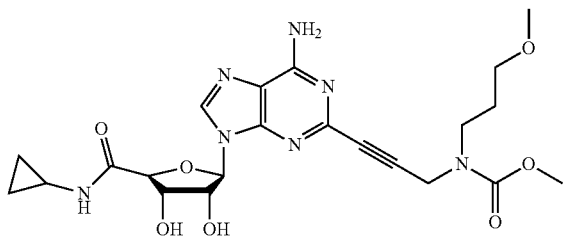

Using the representative procedure for C2-coupling above, N-cyclopropyl 2-iodocarboxamidoadenosine (251 mg) gave the title compound as an off white solid: yield 175 mg, 62%. LRMS ESI (M+H$^+$) 504.2. HPLC rt=9.0 min.

Example 17

N-Cyclopropyl 2-{3-[4-((3-ethoxypropyl)(methoxycarbonyl)amino)]propyn-1-yl}adenosine-5'-uronamide

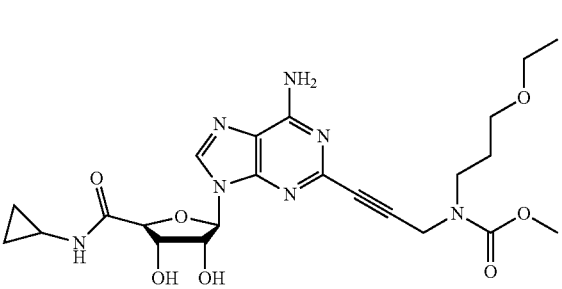

Using the representative procedure for C2-coupling above, N-cyclopropyl 2-iodocarboxamidoadenosine (100 mg) gave the title compound as an off white solid: yield 22 mg, 19%. LRMS ESI (M+H$^+$) 518.2. HPLC rt=9.7 min.

II. Pharmacology

Adenosine $A_{2A}$ Receptor Assays: The ability of a given compound of the invention to act as an adenosine $A_{2A}$ receptor agonist may be determined using pharmacological models which are well known to the art, or using tests described below.

Cell culture and membrane preparation. Sf9 cells were cultured in Grace's medium supplemented with 10% fetal bovine serum, 2.5 µg/ml amphotericin B and 50 µg/ml gentamycin in an atmosphere of 50% $N_2$/50% $O_2$. Viral infection was performed at a density of 2.5×10$^6$ cells/mL with a multiplicity of infection of two for each virus used. Infected cells were harvested 3 days post-infection and washed twice in insect PBS (PBS pH 6.3). Cells were then resuspended in lysis buffer (20 mM HEPES pH 7.5, 150 mM NaCl, 3 mM MgCl$_2$, 1 mM β-mercaptoethanol (BME), 5 µg/mL leupeptin, 5 µg/mL pepstatin A, 1 µg/mL aprotinin, and 0.1 mM PMSF) and snap frozen for storage at −80° C. Cells were thawed on ice, brought to 30 mL total volume in lysis buffer, and burst by $N_2$ cavitation (600 psi for 20 minutes). A low-speed centrifugation was performed to remove any unlysed cells (1000×g for 10 minutes), followed by a high-speed centrifugation (17,000×g for 30 minutes). The pellet from the final centrifugation was homogenized in buffer containing 20 mM HEPES pH 8, 100 mM NaCl, 1% glycerol, 2 µg/mL leupeptin, 2 µg/mL pepstatin A, 2 µg/mL Aprotinin, 0.1 mM PMSF, and 10 µM GDP using a small glass homogenizer followed by passage through a 26 gauge needle. Membranes were aliquoted, snap frozen in liquid $N_2$, and stored at −80° C. Membranes from cells stably expressing the human $A_1$ AR(CHO K1 cells) or $A_3$ AR (HEK 293 cells) were prepared as described (Robeva et al., 1996).

Radioligand Binding Assays. Radioligand binding to recombinant human $A_{2A}$ receptors in Sf9 cell membranes was performed using either the radiolabeled agonist, $^{125}$I-APE (Luthin et al., 1995) or the radiolabeled antagonist, $^{125}$I-ZM241385 ($^{125}$I-ZM). To detect the high affinity, GTPγS-sensitive state of $A_1$ and $A_3$ AR, we used the agonist, $^{125}$I-ABA (Linden et al., 1985; Linden et al., 1993). Binding experiments were performed in triplicate with 5 µg ($A_{2A}$) or 25 µg ($A_1$ and $A_3$) membrane protein in a total volume of 0.1 mL HE buffer (20 mM HEPES and 1 mM EDTA) with1 U/mL adenosine deaminase and 5 mM $MgCl_2$ with or without 50 µM GTPγS. Membranes were incubated with radioligands at room temperature for three hours (for agonists) or two hours (for antagonists) in Millipore Multiscreen® 96-well GF/C filter plates and assays were terminated by rapid filtration on a cell harvester (Brandel, Gaithersburg, Md.) followed by 4×150 µL washes over 30 seconds with ice cold 10 mM Tris-HCl, pH 7.4, 10 mM $MgCl_2$. Nonspecific binding was measured in the presence of 50 µM NECA. Competition binding assays were performed as described (Robeva et al., 1996) using 0.5-1 nM $^{125}$I-APE, $^{125}$I-ZM241385, or $^{125}$I-ABA. Sometimes it is important to change pipette tips following each serial dilution to prevent transfer on tips of potent hydrophobic compounds. The $K_i$ values for competing compound binding to a single site were derived from $IC_{50}$ values with correction for radioligand and competing compound depletion as described previously (Linden, 1982).

Linden J (1982) Calculating the Dissociation Constant of an Unlabeled Compound From the Concentration Required to Displace Radiolabel Binding by 50%. *J Cycl Nucl Res* 8: 163-172.

Linden J, Patel A and Sadek S (1985) [$^{125}$I]Aminobenzyladenosine, a New Radioligand With Improved Specific Binding to Adenosine Receptors in Heart. *Circ Res* 56: 279-284.

Linden J, Taylor H E, Robeva A S, Tucker A L, Stehle J H, Rivkees S A, Fink J S and Reppert S M (1993) Molecular Cloning and Functional Expression of a Sheep $A_3$ Adenosine Receptor with Widespread Tissue Distribution. *Mol Pharmacol* 44: 524-532.

Luthin D R, Olsson R A, Thompson R D, Sawmiller D R and Linden J (1995) Characterization of Two Affinity States of Adenosine $A_{2A}$ Receptors With a New Radioligand, 2-[2-(4-Amino-3-[$^{125}$I]Iodophenyl)Ethylamino] Adenosine. *Mol Pharmacol* 47: 307-313.

Robeva A S, Woodard R, Luthin D R, Taylor H E and Linden J (1996) Double Tagging Recombinant $A_1$- and $A_{2A}$-Adenosine Receptors With Hexahistidine and the FLAG Epitope. Development of an Efficient Generic Protein Purification Procedure. *Biochem Pharmacol* 51: 545-555.

Chemiluminescence Methods: Luminol enhanced chemiluminescence, a measure of neutrophil oxidative activity, is dependent upon both superoxide production and mobilization of the granule enzyme myeloperoxidase. The light is emitted from unstable high-energy oxygen species such as hypochlorous acid and singlet oxygen generated by activated neutrophils.

Purified human neutrophils (2×106/ml) suspended in Hanks balanced salt solution containing 0.1% human serum albumin (HA), adenosine deaminase (1 U/mL) and rolipram (100 nM) were incubated (37 C) in a water bath for 15 min with or without rhTNF (10 U/ml). Following incubation 100 L aliquots of the PMN were transferred to wells (White walled clear bottom 96 well tissue culture plates Costar #3670; 2 wells/condition) containing 501 HA and luminol (final concentration 100M) with or without adenosine agonist (final agonist concentrations 0.01-1000 nM). The plate was incubated 5 min (37 C) and then fMLP (50 1 in HA; final concentration 1M) was added to all wells.

Peak chemiluminescence was determined with a Victor 1420 Multilabel Counter in the chemiluminescence mode using the Wallac Workstation software. Data are presented as peak chemiluminescence as percent of activity in the absence of an adenosine agonist. The $EC_{50}$ was determined using PRISM software. All compounds were tested with PMNs from three separate donors.

Effect of $A_{2A}$ Agonists on Neutrophil Oxidative Activity: f-met-leu-phe (fMLP), luminol, superoxide dismutase, cytochrome C, fibrinogen, adenosine deaminase, and trypan blue were obtained from Sigma Chemical. Ficoll-hypaque was purchased from ICN (Aurora, Ohio), and Cardinal Scientific (Santa Fe, N. Mex.) and Accurate Chemicals and Scientific (Westerbury, N.Y.). Endotoxin (lipopolysaccharide; *E. coli* K235) was from List Biologicals (Campbell, Calif.). Hanks balanced salt solution (HBSS), and *limulus amebocyte* lysate assay kit were from BioWittaker (Walkersville, Md.). Human serum albumin (HSA) was from Cutter Biological (Elkhart, Ind.). Recombinant human tumor necrosis factor-α was supplied by Dianippon Pharmaceutical Co. Ltd. (Osaka, Japan). ZM241385 (4-(2-[7-amino-2-(2-furyl)[1,2,4]triazolo[2,3-a][1,3,5]triazin-5-yl amino]ethyl)phenol) was a gift from Simon Poucher, Zeneca Pharmaceuticals, Cheshire, UK. Stock solutions (1 mM and 10 mM in DMSO) were made and stored at −20° C.

Human neutrophil preparation: Purified neutrophils (98% neutrophils and >95% viable by trypan blue exclusion) containing <1 platelet per 5 neutrophils and <50 pg/ml endotoxin (*limulus amebocyte* lysate assay) were obtained from normal heparinized (10 U/ml) venous blood by a one step Ficoll-hypaque separation procedure (A. Ferrante et al., *J. Immunol. Meth.*, 36, 109 (1980)).

Release of inflammatory reactive oxygen species from primed and stimulated human neutrophils Chemiluminescence: Luminol-enhanced chemiluminescence, a measure of neutrophil oxidative activity, is dependent upon both superoxide production and mobilization of the lysosomal granule enzyme myeloperoxidase. The light is emitted from unstable high-energy oxygen species generated by activated neutrophils. Purified neutrophils (5–10×10$^5$/ml) were incubated in Hanks balanced salt solution containing 0.1% human serum albumin (1 ml) with the tested $A_{2A}$ agonist with or without rolipram and with or without tumor necrosis factor α; (1 U/ml) for 30 minutes at 37° C. in a shaking water bath. Then luminol (1×10$^{-4}$ M) enhanced f-met-leu-phe (1 mcM) stimulated chemiluminescence was read with a Chronolog® Photometer (Cronolog Corp., Havertown, Pa.) at 37° C. for 2-4 minutes. Chemiluminescence is reported as relative peak light emitted (=height of the curve) compared to samples with tumor necrosis factor-α and without agonist or rolipram.

Representative compounds of the present invention have been shown to be active in the above affinity testing. Table 3 provides the results from the binding assays and the oxidative activity assays.

TABLE 3

| Compound | $A_{2A}$ Binding Activity* | Functional Activity* |
|---|---|---|
| Example 1 | High Potency | High Potency |
| Example 2 | High Potency | High Potency |
| Example 3 | High Potency | High Potency |
| Example 4 | Medium Potency | High Potency |
| Example 5 | Not tested | Not tested |
| Example 6 | High Potency | High Potency |
| Example 7 | High Potency | High Potency |
| Example 8 | High Potency | High Potency |
| Example 9 | High Potency | High Potency |
| Example 10 | Medium Potency | Low Potency |
| Example 11 | High Potency | High Potency |
| Example 12 | High Potency | High Potency |
| Example 13 | Medium Potency | High Potency |

TABLE 3-continued

| Compound | $A_{2A}$ Binding Activity* | Functional Activity* |
| --- | --- | --- |
| Example 14 | High Potency | High Potency |
| Example 15 | High Potency | High Potency |
| Example 16 | Medium Potency | High Potency |
| Example 17 | Medium Potency | Low Potency |

*Activity:
<10 nM High Potency
11 to 100 nM Medium Potency
>100 nM Low Potency

Intraocular Pressure Assay: This example illustrates that the select compounds exhibit an intraocular pressure lowering effect in a model for intraocular pressure reduction and demonstrates that these compounds may be useful as a preventive or therapeutic agent for glaucoma or ocular hypertension.

(1) Test for intraocular pressure reduction using Japanese white rabbits: In order to examine the usefulness of the present compound as a preventive or therapeutic agent for glaucoma or ocular hypertension, an intraocular pressure lowering effect when the present compound was administered to Japanese white rabbits (sex: male) was evaluated and studied. As the test compound, Compound A was used.

Preparation of Test Liquid: According to the Preparation Method for an Eye Drop described above, a test liquid containing Compound A (0.01% (w/v) was prepared. Specifically, to 10 mM phosphate buffer or 1.7% borate buffer, polysorbate 80 and the test compound was added and dissolved or dispersed therein. Then, the pH of the resulting solution or dispersion was adjusted to 5 with sodium hydroxide and/or dilute hydrochloric acid, whereby a test liquid containing the test compound was prepared.

Administration method and measurement method: Just before any of the test liquids was administered, one drop of 0.4% oxybuprocaine hydrochloride eye drop was instilled into both eyes of each experimental animal to achieve local anesthesia, and the intraocular pressure was measured using an applanation tonometer. This intraocular pressure was determined as an initial intraocular pressure.

Any of the prepared test liquids was administered into one eye of each experimental animal in a single dose. The other eye was left untreated, or a vehicle was instilled into the eye according to the same schedule.

After the test liquid was administered, the intraocular pressure of both eyes of each experimental animal was measured at predetermined times (at 1, 2, 4 and 6 hours after administration). Incidentally, before measurement, one drop of 0.4% oxybuprocaine hydrochloride eye drop was instilled into both eyes of each experimental animal to achieve local anesthesia.

Calculation of intraocular pressure reduction degree: The intraocular pressure reduction degree of each test compound administration group at each measurement time was calculated from the following calculation formula. Among the obtained intraocular pressure reduction degrees at respective measurement times, the maximum value was determined as a maximum intraocular pressure reduction degree.

$$\text{Intraocular pressure reduction degree (mmHg)} = |\text{IOP}(Ad\text{-}t) - \text{IOP}(Ad\text{-}0)| \quad \text{Equation 2:}$$

IOP (Ad-t): Intraocular pressure of the eye into which the test compound was administered at t hours after administration of test compound.

IOP (Ad-0): Initial intraocular pressure of the eye into which the test compound was administered Results and discussion: The test result (maximum intraocular pressure reduction degree (mmHg)) in the case of using Compound A is shown in Table 4. As is apparent from Table 2, the compound exhibited an intraocular pressure lowering action.

TABLE 4

| Test Compound | Maximum intraocular pressure reduction degree (mmHg) |
| --- | --- |
| Compound A | 3.9 |

*The maximum intraocular pressure reduction degree is represented by the average value for each group consisting of 5 cases.

III. Preparation Examples

A therapeutic agent as described herein will be more specifically described with reference to preparation examples, however, the invention is not limited only to these preparation examples.

Preparation Example 1

Eye Drop

| In 100 ml, | |
| --- | --- |
| Compound A | 0.1 g |
| Concentrated glycerin | 2.6 g |
| Sodium dihydrogen phosphate | q.s. |
| Polysorbate 80 | q.s. |
| Sodium hydroxide | q.s. |
| Dilute hydrochloric acid | q.s. |
| Sterile purified water | q.s. |

To sterile purified water, Compound A and the other components described above are added, and these components are well mixed, whereby an eye drop is prepared. By changing the amount of Compound A to be added, an eye drop at a concentration of 0.01% (w/v), 0.03% (w/v), 0.05% (w/v), or 0.3% (w/v) can be prepared.

Preparation Example 2

Eye Drop

| In 100 ml | |
| --- | --- |
| Compound A | 0.1 g |
| Boric acid | 2.0 g |
| Polysorbate 80 | q.s. |
| Sodium hydroxide | q.s. |
| Dilute hydrochloric acid | q.s. |
| Sterile purified water | q.s. |

To sterile purified water, Compound A and the other components described above are added, and these components are well mixed, whereby an eye drop is prepared. By changing the amount of Compound A to be added, an eye drop at a concentration of 0.01% (w/v), 0.03% (w/v), 0.05% (w/v), or 0.3% (w/v) can be prepared.

Any embodiment or feature of the present invention whether characterized as preferred or not characterized as preferred may be combined with any other aspect or feature of the invention, whether such other feature is characterized as preferred or not characterized as preferred.

Numerous modifications and variations of the present invention are possible in light of the above teachings. It is therefore to be understood that within the scope of the appended claims, the invention may be practiced otherwise that as specifically described herein.

The invention claimed is:

1. A compound of formula Ia:

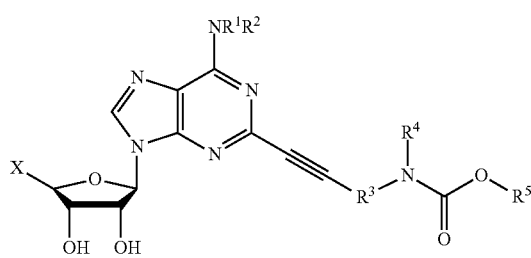

wherein:
- $R^1$ and $R^2$ independently are selected from: H, $C_{1-8}$ alkyl, $C_{3-8}$ cycloalkyl, $(C_{3-8}$ cycloalkyl$)C_{1-8}$ alkyl-, $C_{4-10}$ heterocycle, $(C_{4-10}$ heterocycle$)C_{1-8}$ alkyl-, $C_{6-10}$ aryl, $(C_{6-10}$ aryl$)C_{1-8}$ alkyl-, $C_{5-10}$ heteroaryl, and $(C_{5-10}$ heteroaryl$)C_{1-8}$ alkyl-;
- $R^3$ is —$C_{1-8}$ alkyl-;
- $R^4$ is independently selected from: H, —$C_{2-6}$ alkyl-$OR^a$, —$C_{2-6}$ alkyl-$NR^aR^b$, $C_{1-10}$ alkyl, $C_{3-8}$ cycloalkyl, $(C_{3-8}$ cycloalkyl$)C_{1-8}$ alkyl-, $C_{6-10}$ aryl, $(C_{6-10}$ aryl$)C_{1-8}$ alkyl-, $C_{5-10}$ heteroaryl, and $(C_{5-10}$ heteroaryl$)C_{1-8}$ alkyl-;
- $R^5$ is selected from: $C_{1-8}$ alkyl, —$C_{2-6}$ alkyl-$NR^aR^b$, $C_{3-8}$ cycloalkyl, $(C_{3-8}$ cycloalkyl$)C_{1-8}$ alkyl-, $C_{4-10}$ heterocycle, $(C_{4-10}$ heterocycle$)C_{1-8}$ alkyl-, $C_{6-10}$ aryl, $(C_{6-10}$ aryl$)C_{1-8}$ alkyl-, $C_{5-10}$ heteroaryl, —$C_{2-6}$ alkyl-$OR^a$ and $(C_{5-10}$ heteroaryl$)C_{1-8}$ alkyl-;
- X is selected from: —$CH_2OR^c$, —$OCO_2R^c$, —$OCH_2OC(O)R^c$, —$C(O)NR^cR^d$, —$CH_2SR^c$, —$C(S)OR^c$, —$CH_2OC(S)R^c$, $C(S)NR^cR^d$ and —$CH_2NR^cR^d$; or X is a $C_{5-6}$ heteroaryl;
- $R^a$ and $R^b$ are each independently selected from H, $C_{1-8}$ alkyl, $(C_{1-8}$ alkoxy$)_{1-3}C_{1-8}$ alkyl-, $C_{3-8}$ cycloalkyl, $(C_{3-8}$ cycloalkyl$)C_{1-8}$ alkyl-, $C_{6-10}$ aryl, $(C_{6-10}$ aryl$)C_{1-8}$ alkyl-, $C_{5-10}$ heteroaryl, and $(C_{5-10}$ heteroaryl$)C_{1-8}$ alkyl-; or $R^a$ and $R^b$, together with the nitrogen to which they are attached, form a ring selected from pyrrolidino, piperidino, morpholino, and thiomorpholino ring;
- $R^c$ is selected from: H, $C_{1-8}$ alkyl, $C_{3-6}$ cycloalkyl, and $(C_{3-6}$ cycloalkyl$)C_{1-8}$ alkyl-; and
- $R^d$ is selected from: H, $C_{1-8}$ alkyl, $(C_{1-8}$ alkoxy$)_{1-3}C_{1-8}$ alkyl-, $C_{3-8}$ cycloalkyl, $C_{6-10}$ aryl, $(C_{6-10}$ aryl$)C_{1-8}$ alkyl-, $C_{5-10}$ heteroaryl, and $(C_{5-10}$ heteroaryl$)C_{1-8}$ alkyl-; and stereoisomers or pharmaceutically acceptable salts thereof.

2. The compound of claim 1, wherein $R^1$ and $R^2$ are each hydrogen.

3. The compound of claim 2, wherein $R^3$ is $C_1$ alkyl.

4. The compound of claim 3, wherein X is —$C(O)NR^cR^d$.

5. The compound of claim 4, wherein $R^c$ is hydrogen.

6. The compound of claim 4, wherein $R^d$ is $C_{1-8}$ alkyl, $R^4$ is $C_{1-10}$ alkyl and $R^5$ is $C_{1-8}$ alkyl.

7. The compound of claim 5, wherein $R^d$ is $C_{3-8}$ cycloalkyl.

8. The compound of claim 7, wherein said cycloalkyl is $C_3$ cycloalkyl.

9. The compound of claim 7, wherein $R^5$ is $C_{1-8}$ alkyl.

10. The compound of claim 9, wherein said alkyl is $C_1$ alkyl.

11. The compound of claim 9, wherein $R^4$ is selected from $C_{3-8}$ cycloalkyl, $C_{1-10}$ alkyl and $(C_{6-10}$ aryl$)C_{1-8}$ alkyl-.

12. The compound of claim 11, wherein said $C_{1-10}$ alkyl is a $C_1$, $C_2$, $C_3$ or $C_4$ alkyl.

13. The compound of claim 12, wherein said $C_{1-10}$ alkyl is methyl.

14. The compound of claim 13, wherein said methyl is unsubstituted or substituted with aryl or cycloalkyl.

15. The compound of claim 7, wherein $R^4$ is $C_{1-10}$ alkyl.

16. The compound of claim 15, wherein said alkyl is $C_1$ alkyl.

17. The compound of claim 15, wherein $R^5$ is selected from $C_{6-10}$ aryl and —$C_{2-6}$ alkyl-$OR^a$.

18. The compound of claim 1, wherein said compound is selected from:

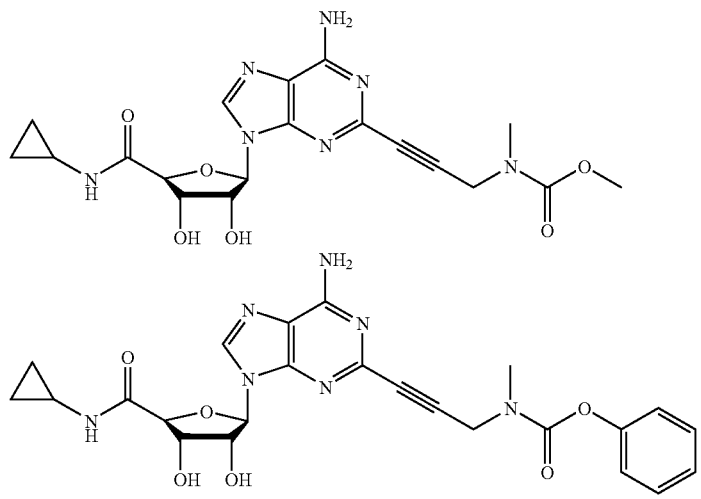

-continued
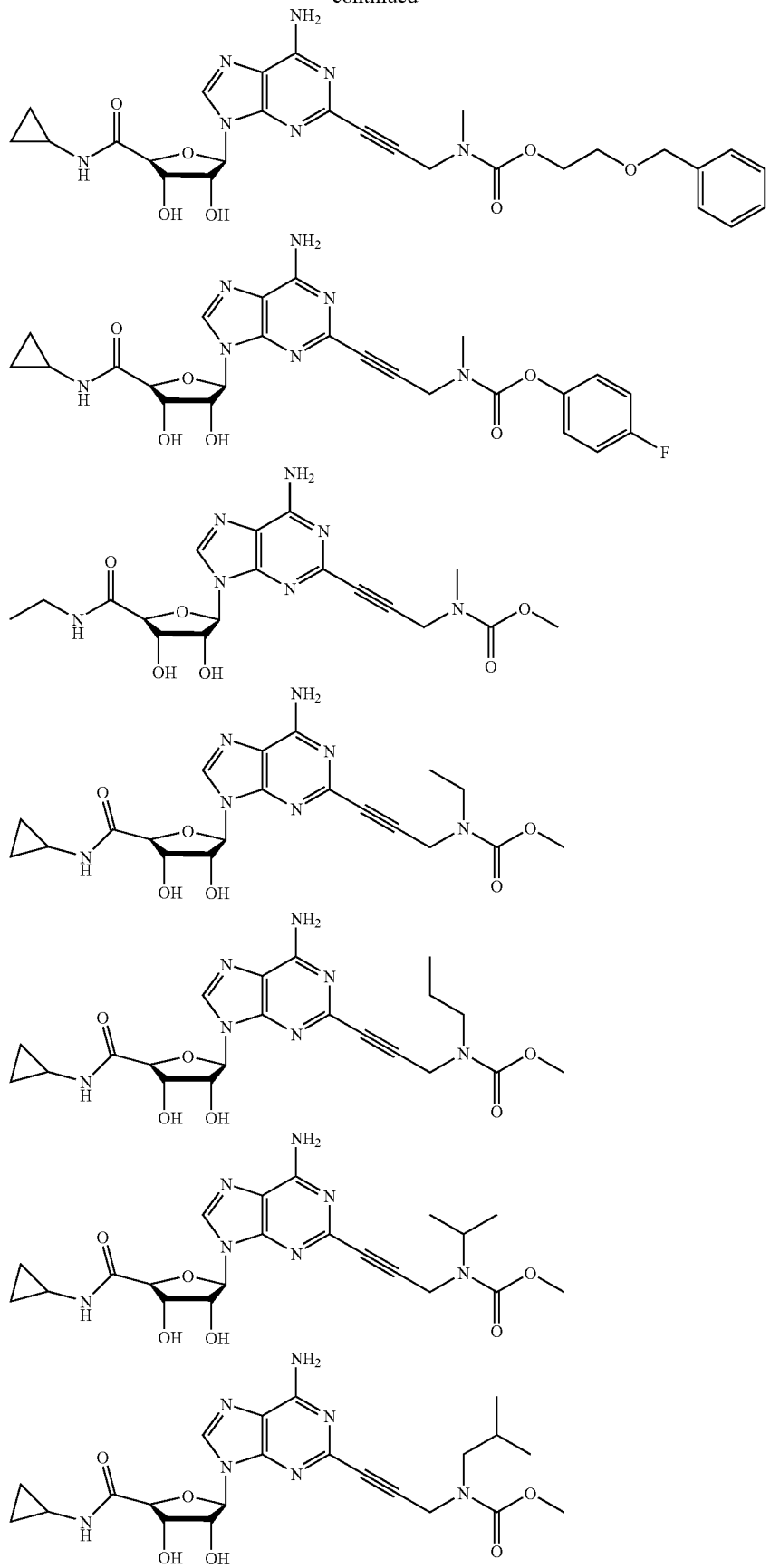

-continued
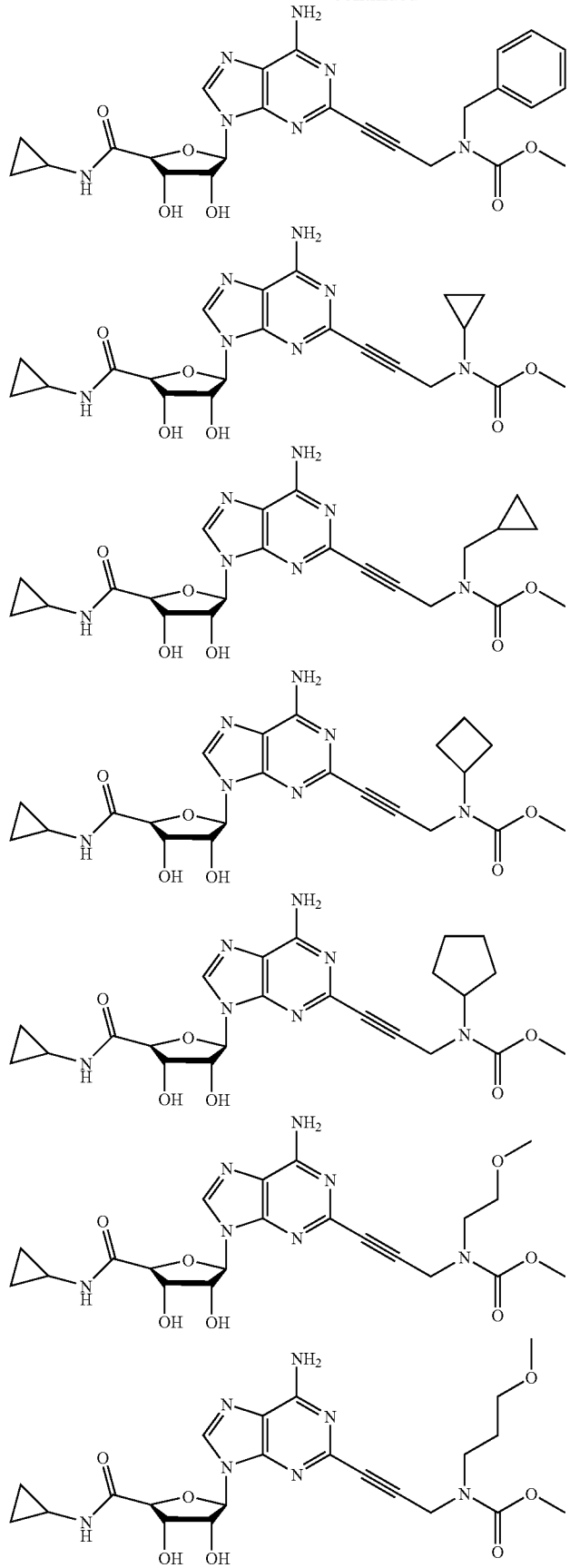

-continued

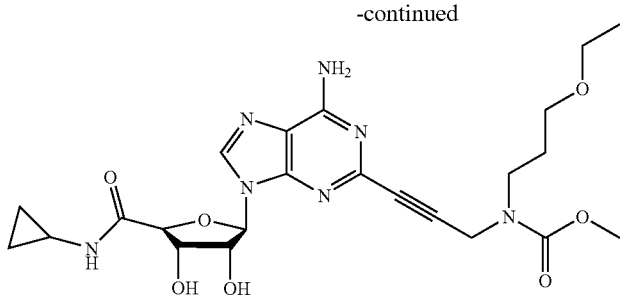

and pharmaceutically acceptable salts thereof.

19. The compound of claim 1, wherein said compound of formula Ia is a compound of formula I:

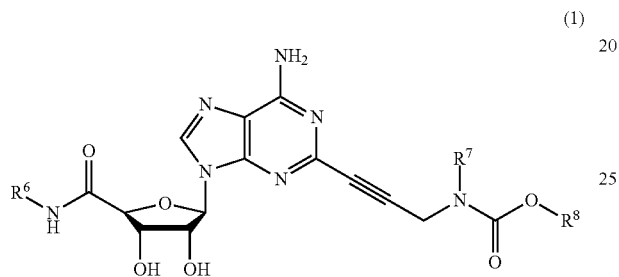

wherein
- $R^6$ is hydrogen, $C_{1-8}$ alkyl, or $C_{3-6}$ cycloalkyl;
- $R^7$ is hydrogen atom or $C_{1-10}$ alkyl;
- $R^8$ is $C_{1-8}$ alkyl, $C_{3-8}$ cycloalkyl, unsubstituted phenyl, or a phenyl substituted with at least a halogen atom or -G-O-$R^9$;
- $R^9$ is alkyl, cycloalkyl, phenyl, (cycloalkyl)alkyl, or (phenyl)alkyl; and G is alkylene;

or a pharmaceutically acceptable salt thereof.

20. The compound of claim 19, wherein $R^6$ is a cycloalkyl.
21. The compound of claim 20, wherein $R^7$ is alkyl.
22. The compound of claim 21, wherein $R^8$ is alkyl.
23. A compound of formula Ib:

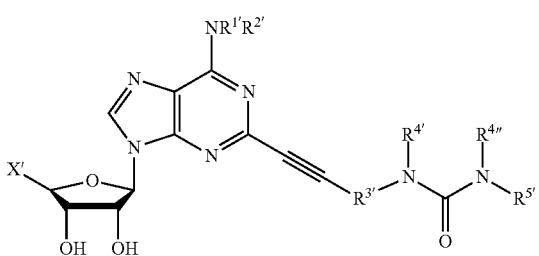

wherein:
- $R^{1'}$ and $R^{2'}$ independently are selected from: H, $C_{1-8}$ alkyl, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;
- $R^{3'}$ is —$C_{1-8}$ alkyl-;
- $R^{4'}$ and $R^{4''}$ are independently selected from: H, —$C_{2-6}$ alkyl-O$R^{a'}$, —$C_{2-6}$ alkyl-N$R^{a'}R^{b'}$, $C_{1-10}$ alkyl, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;
- $R^{5'}$ is selected from: $C_{1-8}$ alkyl, —$C_{2-6}$ alkyl-N$R^{a'}R^{b'}$, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, —$C_{2-6}$ alkyl-O$R^{a'}$ and ($C_{5-10}$ heteroaryl)$C_{1-8}$ alkyl-;
- X' is selected from: —$CH_2OR^{c'}$, —$OCO_2R^{c'}$, —$OCH_2OC(O)R^{c'}$, —$C(O)NR^{c'}R^{d'}$, —$CH_2SR^{c'}$, —$C(S)OR^{c'}$, —$CH_2OC(S)R^{c'}$, $C(S)NR^{c'}R^{d'}$ and —$CH_2NR^{c'}R^{d'}$; or X' is a $C_{5-6}$ heteroaryl;
- $R^{a'}$ and $R^{b'}$ are each independently selected from H, $C_{1-8}$ alkyl, ($C_{1-8}$ alkoxy)$_{1-3}C_{1-8}$ alkyl-, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; or $R^{a'}$ and $R^{b'}$, together with the nitrogen to which they are attached, form a ring selected from pyrrolidino, piperidino, morpholino, and thiomorpholino ring;
- $R^{c'}$ is selected from: H, $C_{1-8}$ alkyl, $C_{3-6}$ cycloalkyl, and ($C_{3-6}$ cycloalkyl)$C_{1-8}$ alkyl-; and
- $R^{d'}$ is selected from: H, $C_{1-8}$ alkyl, ($C_{1-8}$ alkoxy)$_{1-3}C_{1-8}$ alkyl-, $C_{3-8}$ cycloalkyl, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; and stereoisomers or pharmaceutically acceptable salts thereof.

24. A pharmaceutical composition comprising an effective amount of a compound of claim 1 or claim 23 and a pharmaceutically acceptable excipient.

25. The pharmaceutical composition of claim 24, wherein said effective amount is effective to treat an adenosine $A_{2A}$ receptor associated state in a subject.

26. The composition of claim 24, wherein said pharmaceutically composition is formulated for delivery to the eyes.

27. A method for achieving an effect in a subject comprising administering to the subject an effective amount of a compound of formula Ia:

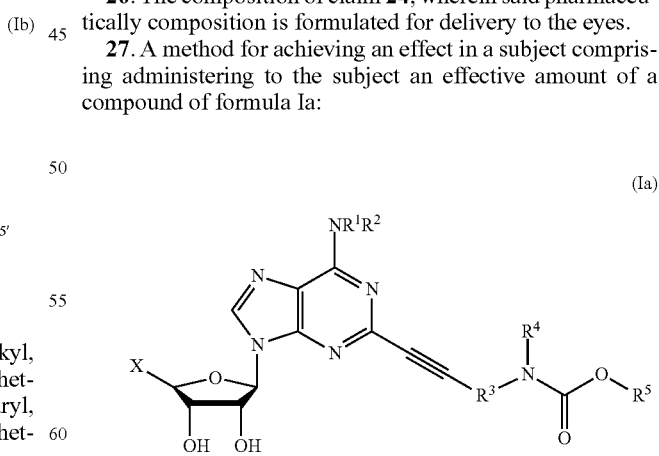

wherein:
- $R^1$ and $R^2$ independently are selected from: H, $C_{1-8}$ alkyl, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;

$R^3$ is —$C_{1-8}$ alkyl-;

$R^4$ is independently selected from: H, —$C_{2-6}$ alkyl-$OR^a$, —$C_{2-6}$ alkyl-$NR^aR^b$, $C_{1-10}$ alkyl, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;

$R^5$ is selected from: $C_{1-8}$ alkyl, —$C_{2-6}$ alkyl-$NR^aR^b$, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, —$C_{2-6}$ alkyl-$OR^a$ and ($C_{5-10}$ heteroaryl)$C_{1-8}$ alkyl-;

X is selected from: —$CH_2OR^c$, —$OCO_2R^c$, —$OCH_2OC(O)R^c$, —$C(O)NR^cR^d$, —$CH_2SR^c$, —$C(S)OR^c$, —$CH_2OC(S)R^c$, $C(S)NR^cR^d$ and —$CH_2NR^cR^d$; or X is a $C_{5-6}$ heteroaryl;

$R^a$ and $R^b$ are each independently selected from H, $C_{1-8}$ alkyl, ($C_{1-8}$ alkoxy)$_{1-3}C_{1-8}$ alkyl-, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; or $R^a$ and $R^b$, together with the nitrogen to which they are attached, form a ring selected from pyrrolidino, piperidino, morpholino, and thiomorpholino ring;

$R^c$ is selected from: H, $C_{1-8}$ alkyl, $C_{3-6}$ cycloalkyl, and ($C_{3-6}$ cycloalkyl)$C_{1-8}$ alkyl-; and $R^d$ is selected from: H, $C_{1-8}$ alkyl, ($C_{1-8}$ alkoxy)$_{1-3}C_{1-8}$ alkyl-, $C_{3-8}$ cycloalkyl, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; and stereoisomers or pharmaceutically acceptable salts thereof, wherein the effect is $A_{2A}$ receptor agonism.

28. A method for achieving an effect in a subject comprising administering to the subject an effective amount of a compound of formula Ib

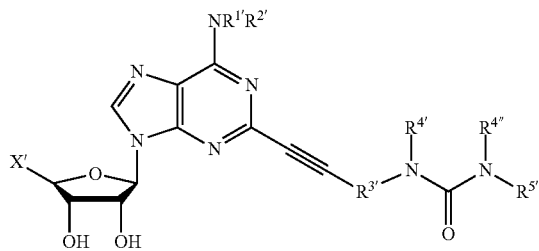

(Ib)

wherein:

$R^{1'}$ and $R^{2'}$ independently are selected from: H, $C_{1-8}$ alkyl, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;

$R^{3'}$ is —$C_{1-8}$ alkyl-;

$R^{4'}$ and $R^{4''}$ are independently selected from: H, —$C_{2-6}$-alkyl-$OR^{a'}$, $C_{2-6}$ alkyl-$NR^{a'}R^{b'}$, $C_{1-10}$ alkyl, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;

$R^{5'}$ is selected from: $C_{1-8}$ alkyl, —$C_{2-6}$ alkyl-$NR^{a'}R^{b'}$, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, —$C_{2-6}$ alkyl-$OR^{a'}$ and ($C_{5-10}$ heteroaryl)$C_{1-8}$ alkyl-;

X' is selected from: —$CH_2OR^{c'}$, —$OCO_2R^{c'}$, —$OCH_2OC(O)R^{c'}$, —$C(O)NR^{c'}R^{d'}$, —$CH_2SR^{c'}$, —$C(S)OR^{c'}$, —$CH_2OC(S)R^{c'}$, $C(S)NR^{c'}R^{d'}$ and —$CH_2NR^{c'}R^{d'}$; or X' is a $C_{5-6}$ heteroaryl;

$R^{a'}$ and $R^{b'}$ are each independently selected from H, $C_{1-8}$ alkyl, ($C_{1-8}$ alkoxy)$_{1-3}C_{1-8}$ alkyl-, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; or $R^{a'}$ and R", together with the nitrogen to which they are attached, form a ring selected from pyrrolidino, piperidino, morpholino, and thiomorpholino ring;

$R^{c'}$ is selected from: H, $C_{1-8}$ alkyl, $C_{3-6}$ cycloalkyl, and ($C_{3-6}$ cycloalkyl)$C_{1-8}$ alkyl-; and $R^{d'}$ is selected from: H, $C_{1-8}$ alkyl, ($C_{1-8}$ alkoxy)$_{1-3}C_{1-8}$ alkyl-, $C_{3-8}$ cycloalkyl, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; and stereoisomers or pharmaceutically acceptable salts thereof, wherein the effect is $A_{2A}$ receptor agonism.

29. The method of claim 27 or 28, wherein said subject has a condition selected from an autoimmune stimulation, inflammation, allergic diseases, skin diseases, infectious diseases, wasting diseases, organ transplantation, tissue or cell transplantation, open wounds, adverse effects from drug therapy, a cardiovascular condition, ischemia-reperfusion injury, gout, chemical trauma, thermal trauma, diabetic nephropathy, sickle cell disease, laminitis, founder's disease, glaucoma, and ocular hypertension.

30. The method of claim 29, wherein said condition is glaucoma or ocular hypertension.

31. A method of reducing intraocular pressure in a subject comprising administering to the subject an effective amount of a compound of formula Ia

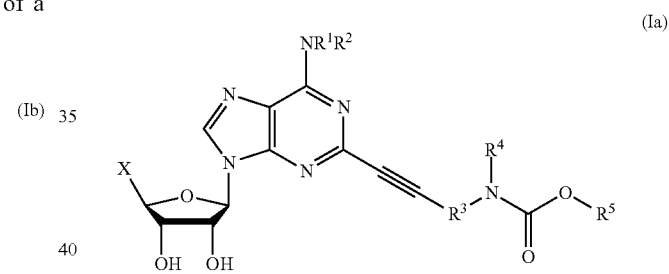

(Ia)

wherein:

$R^1$ and $R^2$ independently are selected from: H, $C_{1-8}$ alkyl, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;

$R^3$ is —$C_{1-8}$ alkyl-;

$R^4$ is independently selected from: H, —$C_{2-6}$ alkyl-$OR^a$, —$C_{2-6}$ alkyl-$NR^aR^b$, $C_{1-10}$ alkyl, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;

$R^5$ is selected from: $C_{1-8}$ alkyl, —$C_{2-6}$ alkyl-$NR^aR^b$, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, —$C_{2-6}$ alkyl-$OR^a$ and ($C_{5-10}$ heteroaryl)$C_{1-8}$ alkyl-;

X is selected from: —$CH_2OR^c$, —$OCO_2R^c$, —$OCH_2OC(O)R^c$, —$C(O)NR^cR^d$, —$CH_2SR^c$, —$C(S)OR^c$, —$CH_2OC(S)R^c$, $C(S)NR^cR^d$ and —$CH_2NR^cR^d$; or X is a $C_{5-6}$ heteroaryl;

$R^a$ and $R^b$ are each independently selected from H, $C_{1-8}$ alkyl, ($C_{1-8}$ alkoxy)$_{1-3}C_{1-8}$ alkyl-, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; or $R^a$ and $R^b$, together with the nitrogen to which they are attached, form a ring selected from pyrrolidino, piperidino, morpholino, and thiomorpholino ring;

$R^c$ is selected from: H, $C_{1-8}$ alkyl, $C_{3-6}$ cycloalkyl, and ($C_{3-6}$ cycloalkyl)$C_{1-8}$ alkyl-; and $R^d$ is selected from: H, $C_{1-8}$ alkyl, ($C_{1-8}$ alkoxy)$_{1-3}C_{1-8}$ alkyl-, $C_{3-8}$ cycloalkyl, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; or stereoisomers or pharmaceutically acceptable salts thereof, formula Ib

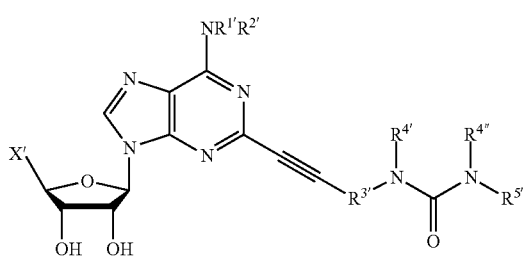

(Ib)

wherein:

$R^{1'}$ and $R^{2'}$ independently are selected from: H, $C_{1-8}$ alkyl, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;

$R^{3'}$ is —$C_{1-8}$ alkyl-;

$R^{4'}$ and $R^{4''}$ are independently selected from: H, —$C_{2-6}$-alkyl-$OR^{a'}$, —$C_{2-6}$ alkyl-$NR^{a'}R^{b'}$, $C_{1-10}$ alkyl, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-;

$R^{5'}$ is selected from: $C_{1-8}$ alkyl, —$C_{2-6}$ alkyl-$NR^{a'}R^{b'}$, $C_{3-8}$ cycloalkyl, ($C_{3-8}$ cycloalkyl)$C_{1-8}$ alkyl-, $C_{4-10}$ heterocycle, ($C_{4-10}$ heterocycle)$C_{1-8}$ alkyl-, $C_{6-10}$ aryl, ($C_{6-10}$ aryl)$C_{1-8}$ alkyl-, $C_{5-10}$ heteroaryl, —$C_{2-6}$ alkyl-$OR^{a'}$ and ($C_{5-10}$ heteroaryl)$C_{1-8}$ alkyl-;

X' is selected from: —$CH_2OR^{c'}$, —$OCO_2R^{c'}$, —$OCH_2OC(O)R^{c'}$, —$C(O)NR^{c'}R^{d'}$, —$CH_2SR^{c'}$, —$C(S)OR^{c'}$, —$CH_2OC(S)R^{c'}$, $C(S)NR^{c'}R^{d'}$ and —$CH_2NR^{c'}R^{d'}$; or X' is a $C_{5-6}$ heteroaryl;

$R^{a'}$ and $R^{b'}$ are each independently selected from H, $C_{1-8}$ alkyl, ($C_{1-8}$ alkoxy)$_{1-3}C_{1-8}$ alkyl-, $C_{3-8}$ cycloalkyl, ($C_{3-8}$ cycloalkyl)$C_{1-8}$ alkyl-, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; or $R^{a'}$ and $R^{b'}$, together with the nitrogen to which they are attached, form a ring selected from pyrrolidino, piperidino, morpholino, and thiomorpholino ring;

$R^{c'}$ is selected from: H, $C_{1-8}$ alkyl, $C_{3-6}$ cycloalkyl, and ($C_{3-6}$ cycloalkyl)$C_{1-8}$ alkyl-; and $R^{d'}$ is selected from: H, $C_{1-8}$ alkyl, ($C_{1-8}$ alkoxy)$_{1-3}C_{1-8}$ alkyl-, $C_{3-8}$ cycloalkyl, $C_{6-10}$ aryl, ($C_{6-10}$ aryl)$C_{1-8}$ alkyl-, $C_{5-10}$ heteroaryl, and ($C_{5-10}$ heteroaryl)$C_{1-8}$ alkyl-; or stereoisomers or pharmaceutically acceptable salts thereof, or formula I

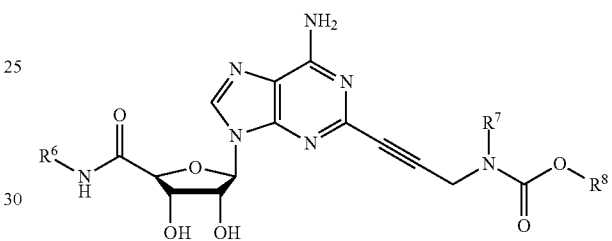

(1)

wherein $R^6$ is hydrogen, $C_{1-8}$ alkyl, or $C_{3-6}$ cycloalkyl, $R^7$ is hydrogen atom or $C_{1-10}$ alkyl;

$R^8$ is $C_{1-8}$ alkyl, $C_{3-8}$ cycloalkyl, unsubstituted phenyl, or a phenyl substituted with at least a halogen atom or -G-O—$R^9$;

$R^9$ is alkyl, cycloalkyl, phenyl, (cycloalkyl)alkyl, or (phenyl)alkyl; and G is alkylene;

or stereoisomers or pharmaceutically acceptable salts thereof, such that the intraocular pressure is reduced.

32. A method of reducing intraocular pressure in a subject according to claim 31 wherein the compound is selected from one or more of the following:

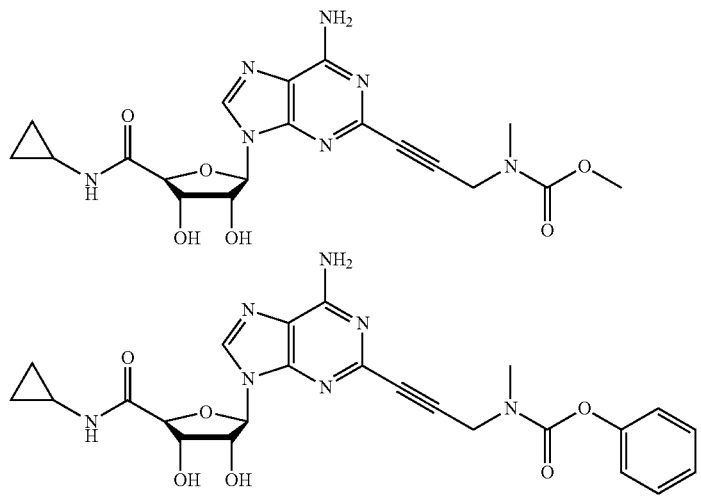

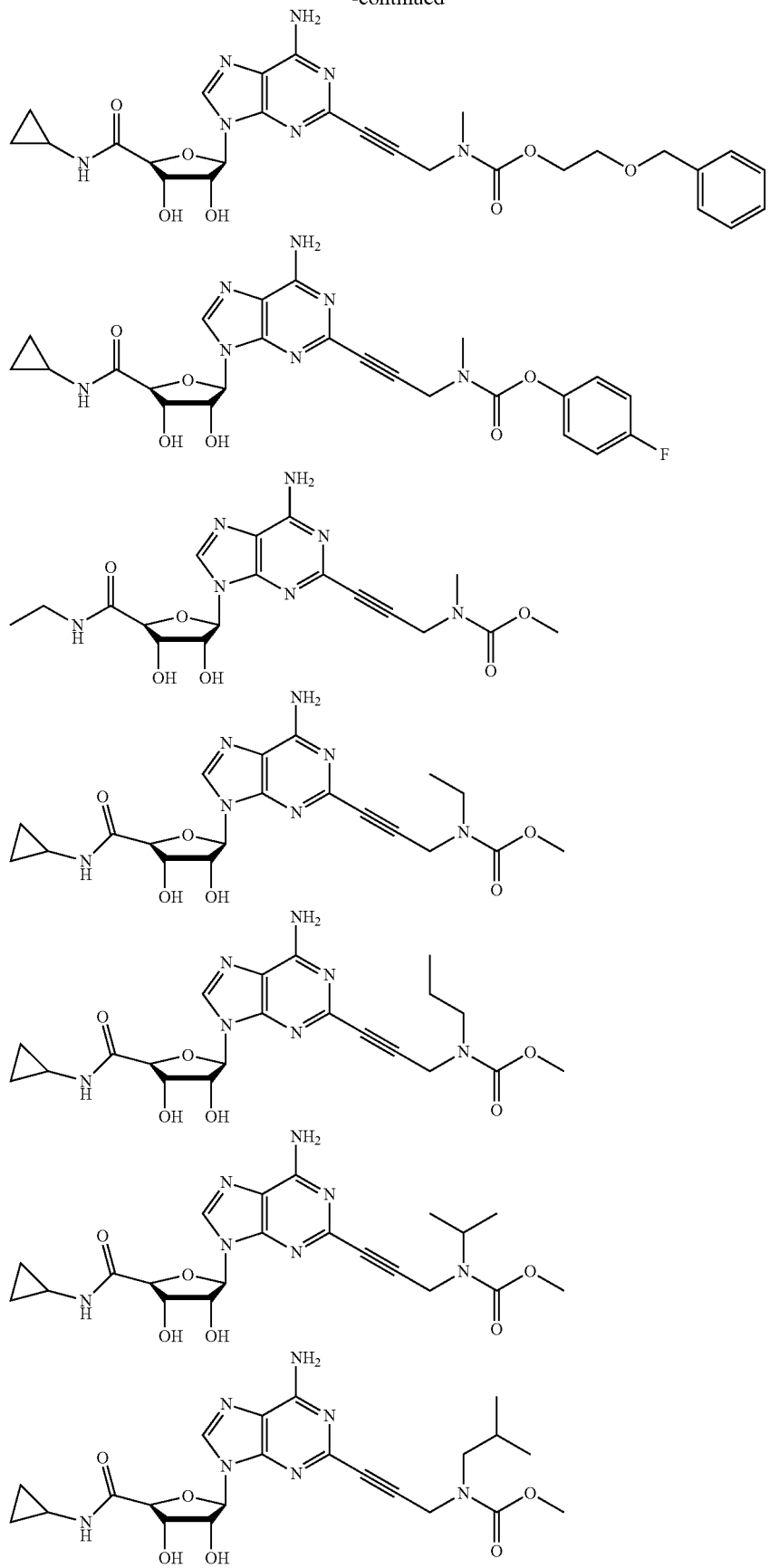

-continued
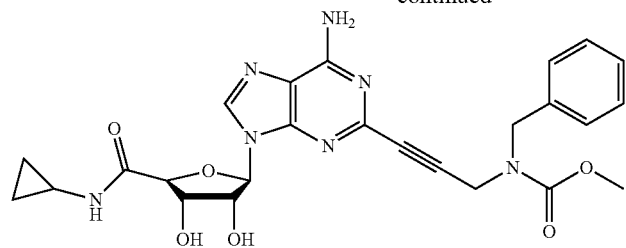
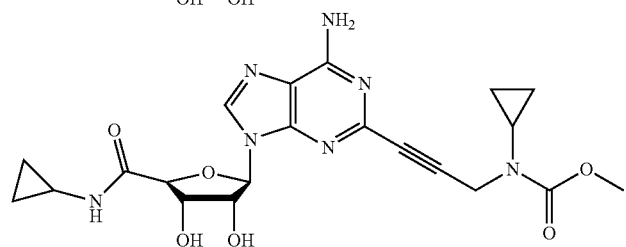
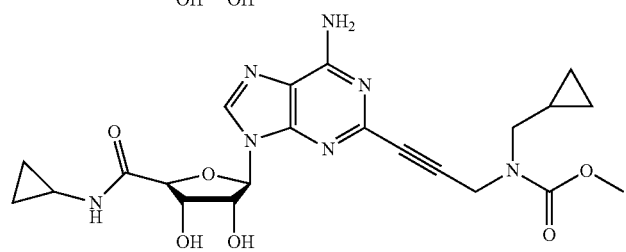
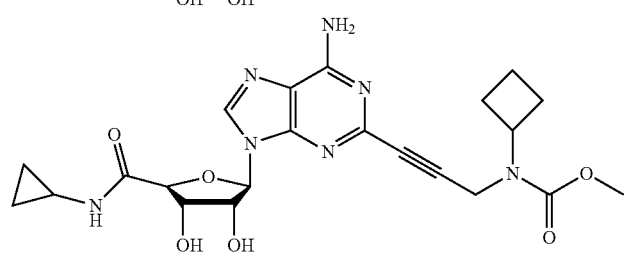
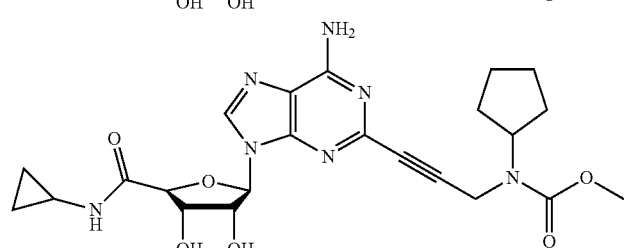
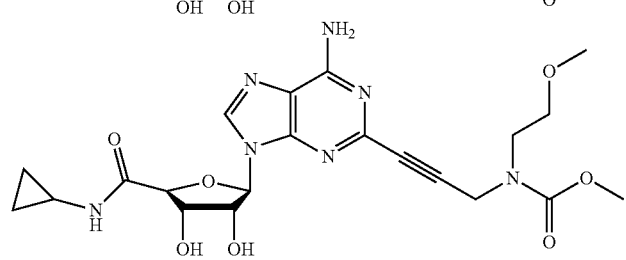
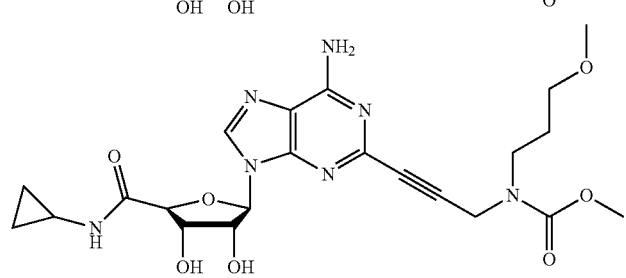

-continued
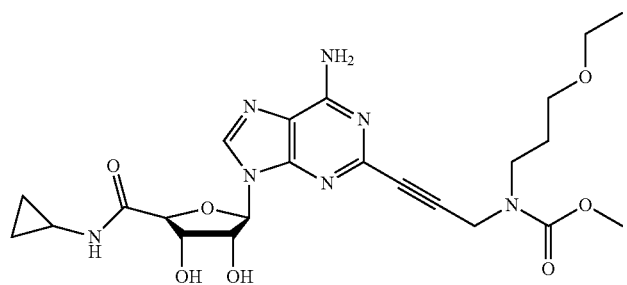
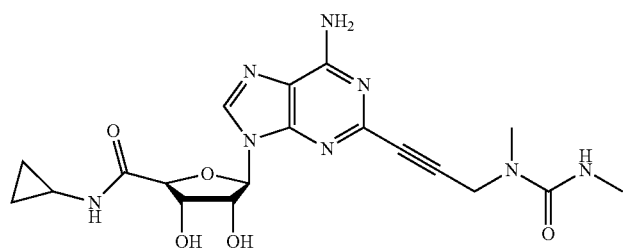
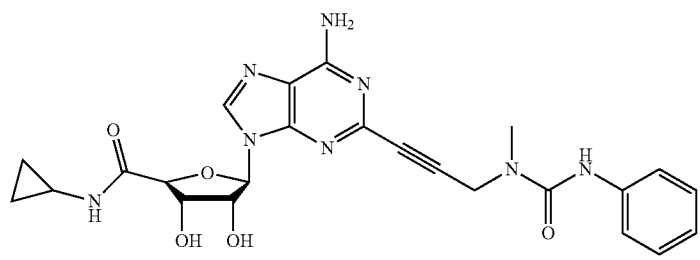
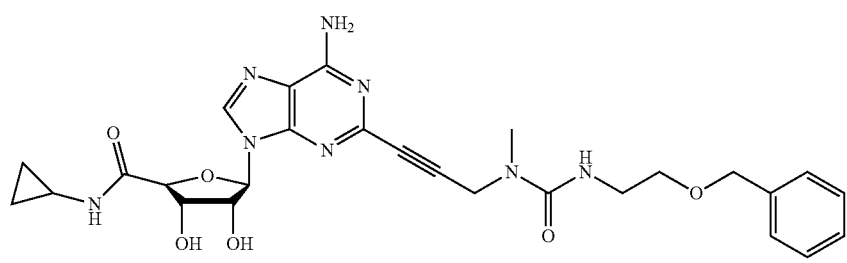
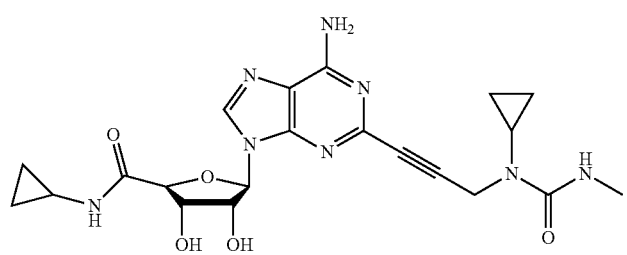
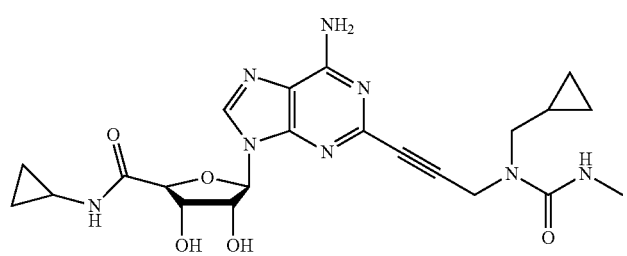

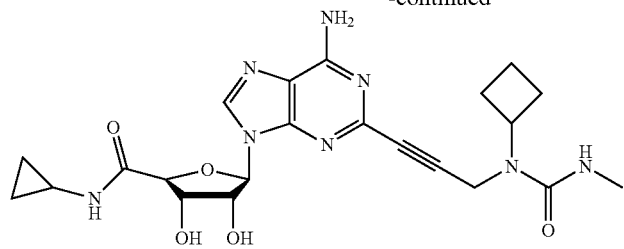
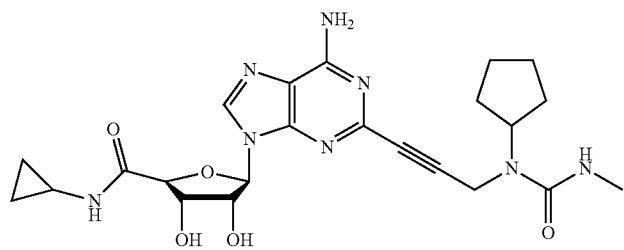
and pharmaceutically acceptable salts thereof.
33. A compound according to claim 23 wherein said compound is selected from:
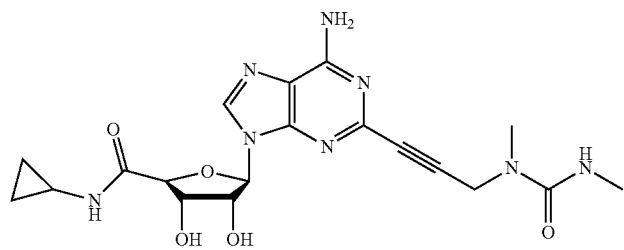
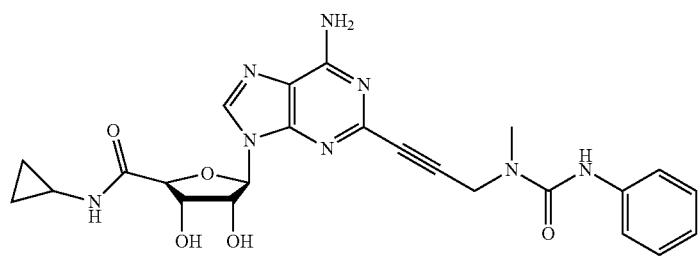
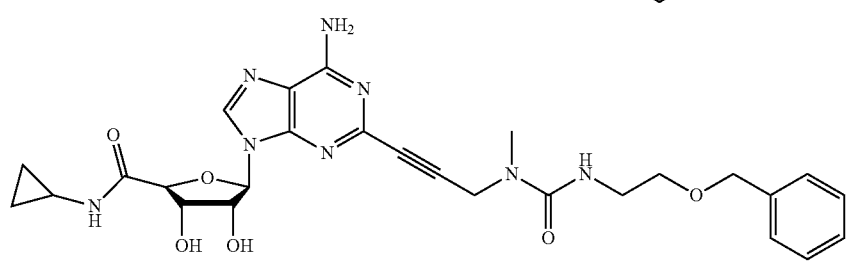
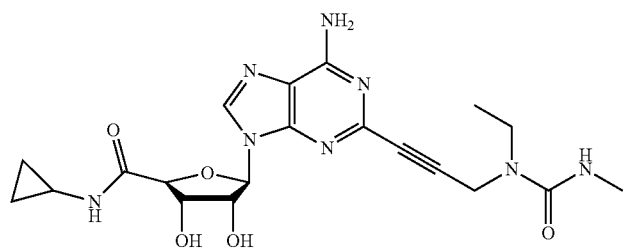

-continued
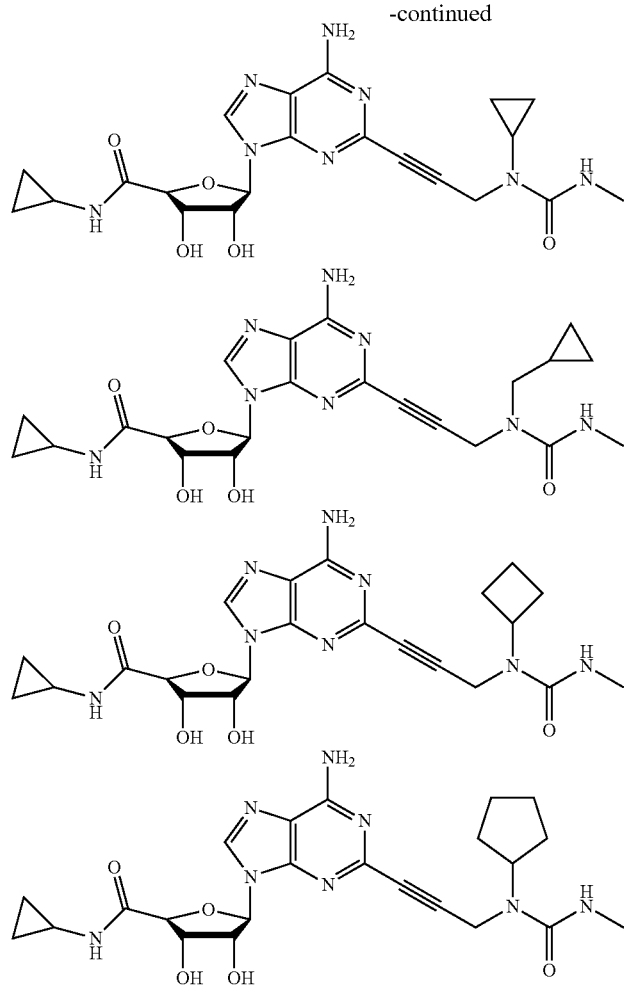
and a pharmaceutically acceptable salt thereof.
* * * * *